(12) United States Patent
Kuball et al.

(10) Patent No.: US 9,891,211 B2
(45) Date of Patent: Feb. 13, 2018

(54) GAMMA 9 DELTA 2 T CELL RECEPTORS

(71) Applicant: UMC UTRECHT Holding B.V., Utrecht (NL)

(72) Inventors: Jürgen Herbert Ernst Kuball, Hilversum (NL); Elsa-Cordula Gründer, Rabenau (DE)

(73) Assignee: Gadeta B.V., Utrecht (NL)

( * ) Notice: Subject to any disclaimer, the term of this patent is extended or adjusted under 35 U.S.C. 154(b) by 0 days.

(21) Appl. No.: 14/388,675

(22) PCT Filed: Mar. 28, 2013

(86) PCT No.: PCT/NL2013/050235
§ 371 (c)(1),
(2) Date: Sep. 26, 2014

(87) PCT Pub. No.: WO2013/147606
PCT Pub. Date: Oct. 3, 2013

(65) Prior Publication Data
US 2015/0050670 A1    Feb. 19, 2015

Related U.S. Application Data

(60) Provisional application No. 61/616,440, filed on Mar. 28, 2012, provisional application No. 61/703,788, filed on Sep. 21, 2012.

(51) Int. Cl.

| | |
|---|---|
| *C07K 14/705* | (2006.01) |
| *G01N 33/50* | (2006.01) |
| *C12N 15/85* | (2006.01) |
| *G01N 33/68* | (2006.01) |
| *A61K 38/00* | (2006.01) |
| *A61K 35/17* | (2015.01) |
| *C07K 14/725* | (2006.01) |

(52) U.S. Cl.
CPC .......... *G01N 33/5011* (2013.01); *A61K 35/17* (2013.01); *C07K 14/7051* (2013.01); *C12N 15/85* (2013.01); *G01N 33/505* (2013.01); *G01N 33/6866* (2013.01); *A61K 38/00* (2013.01)

(58) Field of Classification Search
CPC .... A61K 35/17; A61K 38/00; C07K 14/7051; G01N 33/6866; G01N 33/5011; G01N 33/505; C12N 15/85
See application file for complete search history.

(56) References Cited

U.S. PATENT DOCUMENTS 5,723,309 A    3/1998    Bonneville

FOREIGN PATENT DOCUMENTS

WO    2006056733 A1    6/2006

OTHER PUBLICATIONS

D. Kabelitz et al., "Perspectives of T Cells in Tumor Immunology", Cancer Research, vol. 67, No. 1, pp. 5-8, Jan. 1, 2007, XP055069391.
Fisch, P. et al., "Recognition by Human V-Gamma-9-V-Delta-2 T Cells of a GroEL Homolog on Daudi Burkitt's Lymphoma Cell", vol. 250, No. 4985, pp. 1269-1273, 1990, XP002700183.
Dieter Kabelitz et al., "Potential of Human ?? T Lymphocytes for Immunotherapy of Cancer", International Journal of Cancer, vol. 112, No. 5, pp. 727-732, Dec. 10 2004, XP055069912.
X. Xi et al., "The Recognition of TCR Protein Antigen Does Not Depend on the Hydrophobic I97 Residue of CDR3", International Immunology, vol. 22, No. 4, pp. 299-306, Apr. 1, 2010, XP055069895.
Grunder Cordula et al., "Gamma 9-and Delta 2-CDR3 Domains Regulate Functional Avidity of T Cells Harboring c9d2 T Cell Receptors", Journal of Immunotherapy, vol. 35, No. 9, pp. 723, Nov. 2012, XP002700184.
Moser Bernhard "Tumor-Killing [gamma] [delta]—TCRs take center stage." Blood, vol. 120, No. 26, pp. 5093-5094, Dec. 20, 2012, XP002700185.
Database WPI, Week 201240, Thomson Scientific, London, GB; (Inst Basic Medical Sci Chinese Acad Medi), May 16, 2012, XP002700186.
Straetemans T et al.: "Towards gamma/delta TCR gene therapy: the optimal gamma/delta TCR transgene cassette", Bone Marrow Transplantation, vol. 48 No. Suppl. 2, pp. S72, Apr. 2013, XP002700187.
International Search Report for PCT/NL2013/050235 dated Oct. 9, 2013.
Chunping Xu et al., "γδ T Cells Recognize Tumor Cells Via CDR3δ Region", Molecular Immunology, 2007, vol. 44, pp. 302-310.
Co-pending U.S. Appl. No. 15/374,613, filed Dec. 9, 2016.
Zhao, et al. CDR3δ-grafted γ9δ2T cells mediate effective antitumor reactivity. Cell Mol Immunol. Mar. 2012;9(2):147-54. doi: 10.1038/cmi.2011.28.Epub Sep. 12, 2011.
Marcu-Malina et al., "Redirecting alpha betaT cells against cancer cells by transfer of a broadly tumor-reactive gamma delta T-cell receptor", 2011, Blood 118: 50-59.
Gomes et al., "Targeting gamma delta T Lymphocytes for Cancer Immunotherapy: From Novel Mechanistic Insight to Clinical Application", 2010, Cancer Res. 70: 10024-10027.

(Continued)

*Primary Examiner* — Robert Landsman
(74) *Attorney, Agent, or Firm* — Wilson Sonsini Goodrich & Rosati

(57) ABSTRACT

The current invention provides methods to identify γ9δ2T-cell receptors (γ9δ2TCR) that mediate anti-tumor responses. Surprisingly, it was now found that the CDR3 regions of the γ9-T-cell receptor chain and the δ2-T-Cell receptor chain (δ2TCR chain) are of importance. Based on these findings, combinatorial-γδTCR-chain-exchange (CTE) is proposed as an efficient method for identifying γ9δ2TCRs that mediate anti-tumor responses. Using the method of the invention, specific sequences of the respective γ9TCR and δ2TCR chains were identified that mediate anti-tumor responses. Hence, the invention further provides for specific γ9δ2TCRs, or fragments thereof, that may be used e.g. in diagnostics or treatment of cancer. The invention further provides for nucleic acid sequences, genetic constructs and retroviral vectors that can be used to express the γ9δ2TCRs according to the invention.

19 Claims, 7 Drawing Sheets

(56) References Cited

OTHER PUBLICATIONS

Figure 1:
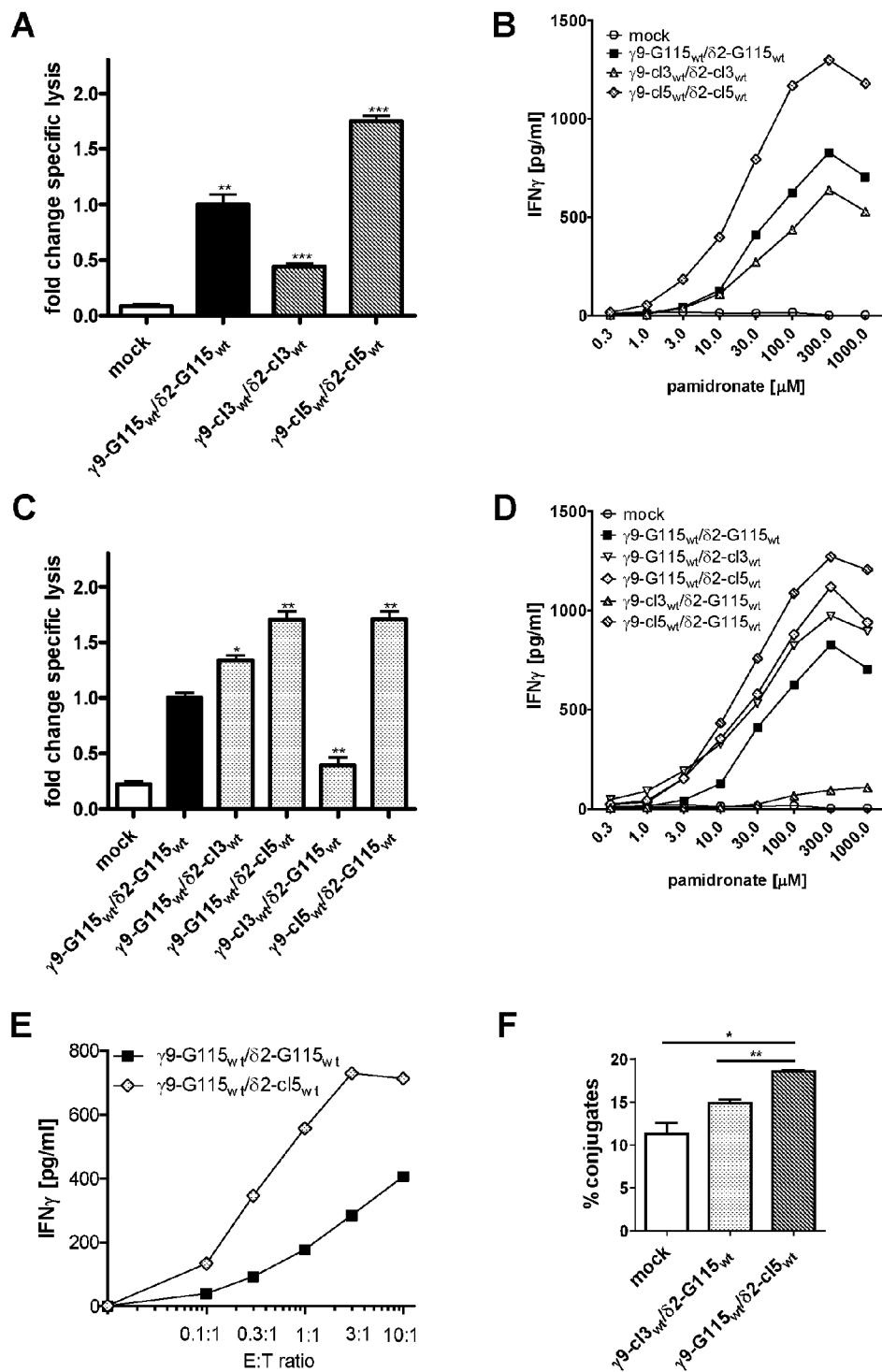

Marcu-Malina et al., "Re-targeting T-cells against cancer by gene-transfer of tumor-reactive receptors", 2009, Expert Opin. Biol. Ther. 9: 579-591.

Castella et al., V gamma 9 V delta 2 T cell-based immunotherapy in hematological malignancies: from bench to bedside, 2011, Cell Miol. Life Sci. 68: 2419-2432.

Nicol et al., "Clinical evaluation of autologous gamma delta T cell-based immunotherapy for metastatic solid tumors", 2011, Br. J. Cancer 105: 778-786.

Bukowski et al., "Crucial Role of TCRgamma Chain Junctional Region in Prenyl Pyrophosphate Antigen Recognition by gamma delta T cells", 1998, J. Immunol. 161: 286-293.

Miyagawa et al., "Essential Contribution of Germline-Encoded Lysine Residues in J gamma1.2 Segment to the Recognition of Nonpeptide Antigens by Human gamma delta T Cells", 2001, J. Immunol. 167: 6773-6779.

Wang et al., "Vgamma2Vdelta2 T Cells Receptor Recognition of Prenyl Pyrophosphates is Dependent on All CDRs", 2010, J. Immunol. 184: 6209-6222.

Born et al., "Peptide antigens for gamma/delta T cells", 2011, Cell Mol. Life Sci., 68: 2335-2343.

Grunder et al., "Gamma-9 and Delta-2CDR3 domains regulate functional avidity of T cells harboring Gamma-9 Delta-2TCRs", 2012, Blood 120: 5153-5162.

Kuball et al., "Avidity maturation of gamma9delta2T-cell receptor engineered T-cells by CDR3 modulation (162.37)", 2012, J. Immunol. 188.

Stanislawski et al., "Circumventing tolerance to a human MDM2-derived tumor antigen by TCR gene transfer", Nat Immunol. 2001; 2(10): 962-970.

Tripodo et al., Gamma-delta T-cell lymphomas, 2009, Nat. Rev. Clin. Oncol. 6: 707-717.

Grunder, et al. Individual T-Cell Receptors of $\gamma9\delta2$T-Cells Mediate Differential Anti-Tumor-reactivity. Abstract Only. From Blood, Nov. 18, 2011; 118: Issue 21, 4312.

Kuball, et al. Increasing functional avidity of TCR-redirected T cells by removing defined N-glycosylation sites in the TCR constant domain. J Exp Med. Feb. 16, 2009;206(2):463-75.

Scheper, et al. 477. Multipotent V$\Delta$2-Negative $\gamma\Delta$T-Cells after CMV-Reactivation in Allogeneic Stem Cell Transplantation. Molecular Therapy. vol. 20, Supplement 1, May 2012, p. S185.

Voss, et al. Designing TCR for Cancer Immunotherapy. Adoptive Immunotherapy: Methods and Protocols pp. 229-256. Part of the Methods in Molecular Medicine™ book series, vol. 109, 2005.

SEQUENCE LISTING

<160> NUMBER OF SEQ ID NOS: 22

<210> SEQ ID NO 1
<211> LENGTH: 315
<212> TYPE: PRT
<213> ORGANISM: Homo sapiens

<400> SEQUENCE: 1

```
Met Val Ser Leu Leu His Ala Ser Thr Leu Ala Val Leu Gly Ala Leu
1               5                   10                  15

Cys Val Tyr Gly Ala Gly His Leu Glu Gln Pro Gln Ile Ser Ser Thr
            20                  25                  30

Lys Thr Leu Ser Lys Thr Ala Arg Leu Glu Cys Val Val Ser Gly Ile
        35                  40                  45

Thr Ile Ser Ala Thr Ser Val Tyr Trp Tyr Arg Glu Arg Pro Gly Glu
    50                  55                  60

Val Ile Gln Phe Leu Val Ser Ile Ser Tyr Asp Gly Thr Val Arg Lys
65                  70                  75                  80

Glu Ser Gly Ile Pro Ser Gly Lys Phe Glu Val Asp Arg Ile Pro Glu
                85                  90                  95

Thr Ser Thr Ser Thr Leu Thr Ile His Asn Val Glu Lys Gln Asp Ile
            100                 105                 110

Ala Thr Tyr Tyr Cys Ala Leu Trp Glu Ala Gln Gln Glu Leu Gly Lys
        115                 120                 125

Lys Ile Lys Val Phe Gly Pro Gly Thr Lys Leu Ile Ile Thr Asp Lys
    130                 135                 140

Gln Leu Asp Ala Asp Val Ser Pro Lys Pro Thr Ile Phe Leu Pro Ser
145                 150                 155                 160

Ile Ala Glu Thr Lys Leu Gln Lys Ala Gly Thr Tyr Leu Cys Leu Leu
                165                 170                 175

Glu Lys Phe Phe Pro Asp Val Ile Lys Ile His Trp Glu Lys Lys
                180                 185                 190
```

```
Ser Asn Thr Ile Leu Gly Ser Gln Glu Gly Asn Thr Met Lys Thr Asn
        195                 200                 205

Asp Thr Tyr Met Lys Phe Ser Trp Leu Thr Val Pro Glu Lys Ser Leu
210                 215                 220

Asp Lys Glu His Arg Cys Ile Val Arg His Glu Asn Asn Lys Asn Gly
225                 230                 235                 240

Val Asp Gln Glu Ile Ile Phe Pro Pro Ile Lys Thr Asp Val Ile Thr
            245                 250                 255

Met Asp Pro Lys Asp Asn Cys Ser Lys Asp Ala Asn Asp Thr Leu Leu
            260                 265                 270

Leu Gln Leu Thr Asn Thr Ser Ala Tyr Tyr Met Tyr Leu Leu Leu Leu
        275                 280                 285

Leu Lys Ser Val Val Tyr Phe Ala Ile Ile Thr Cys Cys Leu Leu Arg
        290                 295                 300

Arg Thr Ala Phe Cys Cys Asn Gly Glu Lys Ser
305                 310                 315

<210> SEQ ID NO 2
<211> LENGTH: 292
<212> TYPE: PRT
<213> ORGANISM: Homo sapiens

<400> SEQUENCE: 2

Met Glu Arg Ile Ser Ser Leu Ile His Leu Ser Leu Phe Trp Ala Gly
1               5                   10                  15

Val Met Ser Ala Ile Glu Leu Val Pro Glu His Gln Thr Val Pro Val
            20                  25                  30

Ser Ile Gly Val Pro Ala Thr Leu Arg Cys Ser Met Lys Gly Glu Ala
        35                  40                  45

Ile Gly Asn Tyr Tyr Ile Asn Trp Tyr Arg Lys Thr Gln Gly Asn Thr
    50                  55                  60

Met Thr Phe Ile Tyr Arg Glu Lys Asp Ile Tyr Gly Pro Gly Phe Lys
65                  70                  75                  80

Asp Asn Phe Gln Gly Asp Ile Asp Ile Ala Lys Asn Leu Ala Val Leu
                85                  90                  95

Lys Ile Leu Ala Pro Ser Glu Arg Asp Glu Gly Ser Tyr Tyr Cys Ala
            100                 105                 110

Cys Asp Thr Leu Gly Met Gly Gly Glu Tyr Thr Asp Lys Leu Ile Phe
        115                 120                 125

Gly Lys Gly Thr Arg Val Thr Val Glu Pro Arg Ser Gln Pro His Thr
    130                 135                 140

Lys Pro Ser Val Phe Val Met Lys Asn Gly Thr Asn Val Ala Cys Leu
145                 150                 155                 160

Val Lys Glu Phe Tyr Pro Lys Asp Ile Arg Ile Asn Leu Val Ser Ser
                165                 170                 175

Lys Lys Ile Thr Glu Phe Asp Pro Ala Ile Val Ile Ser Pro Ser Gly
            180                 185                 190

Lys Tyr Asn Ala Val Lys Leu Gly Lys Tyr Glu Asp Ser Asn Ser Val
        195                 200                 205

Thr Cys Ser Val Gln His Asp Asn Lys Thr Val His Ser Thr Asp Phe
    210                 215                 220

Glu Val Lys Thr Asp Ser Thr Asp His Val Lys Pro Lys Glu Thr Glu
225                 230                 235                 240

Asn Thr Lys Gln Pro Ser Lys Ser Cys His Lys Pro Lys Ala Ile Val
```

```
                 245                 250                 255
His Thr Glu Lys Val Asn Met Met Ser Leu Thr Val Leu Gly Leu Arg
             260                 265                 270

Met Leu Phe Ala Lys Thr Val Ala Val Asn Phe Leu Leu Thr Ala Lys
         275                 280                 285

Leu Phe Phe Leu
    290

<210> SEQ ID NO 3
<211> LENGTH: 16
<212> TYPE: PRT
<213> ORGANISM: Homo Sapiens

<400> SEQUENCE: 3

Ala Leu Trp Glu Ala Gln Gln Glu Leu Gly Lys Lys Ile Lys Val Phe
1               5                  10                  15

<210> SEQ ID NO 4
<211> LENGTH: 16
<212> TYPE: PRT
<213> ORGANISM: Homo Sapiens

<400> SEQUENCE: 4

Ala Cys Asp Thr Leu Gly Met Gly Gly Glu Tyr Thr Asp Lys Leu Ile
1               5                  10                  15

<210> SEQ ID NO 5
<211> LENGTH: 948
<212> TYPE: DNA
<213> ORGANISM: Homo sapiens

<400> SEQUENCE: 5
```

| | | | | |
|---|---|---|---|---|
| atggtgtccc tgctgcacgc cagcaccctg gccgtgctgg gcgccctgtg cgtgtatggc | | | | 60 |
| gccggacacc tggaacagcc ccagatcagc agcaccaaga ccctgagcaa gaccgccagg | | | | 120 |
| ctggaatgcg tggtgtccgg catcaccatc agcgccacct ccgtgtactg gtacagagag | | | | 180 |
| agacccggcg aggtcatcca gttcctggtg tccatcagct acgacggcac cgtgcggaaa | | | | 240 |
| gagagcggca tccccagcgg caagttcgag gtggacagaa tccccgagac cagcacctcc | | | | 300 |
| accctgacca tccacaacgt ggagaagcag gacatcgcca cctactactg cgccctgtgg | | | | 360 |
| gaggcccagc aggaactggg caagaaaatc aaggtgttcg ccctggcac aagctgatc | | | | 420 |
| atcaccgaca gcagctgga cgccgacgtg agccccaagc ctaccatctt cctgcccagc | | | | 480 |
| atcgccgaga ccaagctgca gaaggccggc acctacctgt gcctgctgga aaagttcttc | | | | 540 |
| cccgacgtga tcaagatcca ctgggaggaa aagaagagca caccatcct gggcagccag | | | | 600 |
| gaaggcaata ccatgaaaac caacgacacc tacatgaagt tcagctggct gaccgtgccc | | | | 660 |
| gagaagagcc tggacaaaga gcacagatgc atcgtccggc acgagaacaa caagaacggc | | | | 720 |
| gtggaccagg aaatcatctt cccccccatc aagaccgatg tgatcacaat ggaccccaag | | | | 780 |
| gacaactgca gcaaggacgc caacgatacc ctgctgctgc agctgaccaa caccagcgcc | | | | 840 |
| tactacatgt atctcctgct gctgctgaag agcgtggtgt acttcgccat catcacctgc | | | | 900 |
| tgtctgctgc ggcggaccgc cttctgctgc aacggcgaga agagctga | | | | 948 |

```
<210> SEQ ID NO 6
<211> LENGTH: 879
<212> TYPE: DNA
<213> ORGANISM: Homo sapiens
```

<400> SEQUENCE: 6

```
atggagcgga tcagcagcct gatccacctg agcctgttct gggccggagt gatgagcgcc      60
atcgagctgg tgcccgagca ccagaccgtg cccgtgagca tcggcgtgcc cgccacccty     120
cggtgcagca tgaagggcga ggccatcggc aactactaca tcaactggta cagaaagacc     180
cagggcaaca ccatgacctt catctaccgg gagaaggaca tctacggccc tggcttcaag     240
gacaacttcc agggcgacat cgacatcgcc aagaacctgg ccgtgctgaa gatcctggcc     300
cccagcgaga gggacgaggg cagctactac tgcgcctgcg acaccctggg catgggcggc     360
gagtacaccg acaagctgat cttcggcaag gcacccgggt gaccgtggaa gcccagaagc     420
cagccccaca ccaagcccag cgtgttcgtg atgaagaacg gcaccaacgt ggcctgcctg     480
gtgaaagagt tctaccccaa ggacatccgg atcaacctgg tgtccagcaa gaagatcacc     540
gagttcgacc ccgccatcgt gatcagcccc agcggcaagt acaacgccgt gaagctgggc     600
aagtacgagg acagcaacag cgtgacctgc agcgtgcagc acgacaacaa gaccgtgcac     660
agcaccgact tcgaggtgaa aaccgactcc accgaccacg tgaagcccaa agagaccgag     720
aacaccaagc agcccagcaa gagctgccac aagcccaagg ccatcgtgca caccgagaag     780
gtgaacatga tgagcctgac cgtgctgggc ctgcggatgc tgttcgccaa gacagtggcc     840
gtgaacttcc tgctgaccgc caagctgttc ttcctgtga                            879
```

<210> SEQ ID NO 7
<211> LENGTH: 943
<212> TYPE: DNA
<213> ORGANISM: Homo sapiens

<400> SEQUENCE: 7

```
atggtgtccc tgctgcacgc cagcacccty gccgtgctgg gcgccctgtg cgtgtatggc      60
gccggacacc tggaacagcc ccagatcagc agcaccaaga ccctgagcaa gaccgccagg     120
ctggaatgcg tggtgtccgg catcaccatc agcgccacct ccgtgtactg gtacagagag     180
agacccggcg aggtcatcca gttcctggtg tccatcagct acgacggcac cgtgcggaaa     240
gagagcggca tccccagcgg caagttcgag gtggacagaa tccccgagac cagccacctcc     300
accctgacca tccacaacgt ggagaagcag gacatcgcca cctactactg cgccctgtgg     360
gaggaggaac tgggcaagaa aatcaaggtg ttcggccctg gcaccaagct gatcatcacc     420
gacaagcagc tggacgccga cgtgagcccc aagcctacca tcttcctgcc cagcatcgcc     480
gagaccaagc tgcagaaggc cggcacctac ctgtgcctgc tggaaaagtt cttccccgac     540
gtgatcaaga tccactggga ggaaaagaag agcaacacca tcctgggcag ccaggaaggc     600
aataccatga aaaccaacga cacctacatg aagttcagct ggctgaccgt gcccgagaag     660
agcctggaca aagagcacag atgcatcgtc cggcacgaga acaacaagaa cggcgtggac     720
caggaaatca tcttcccccc catcaagacc gatgtgatca caatggaccc caaggacaac     780
tgcagcaagg acgccaacga tacccctgctg ctgcagctga ccaacaccag cgcctactac     840
atgtatctcc tgctgctgct gaagagcgtg gtgtacttcg ccatcatcac ctgctgtctg     900
ctgcggcgga ccgccttctg ctgcaacggc gagaagagct gag                       943
```

<210> SEQ ID NO 8
<211> LENGTH: 313
<212> TYPE: PRT
<213> ORGANISM: Homo sapiens

<400> SEQUENCE: 8

```
Met Val Ser Leu Leu His Ala Ser Thr Leu Ala Val Leu Gly Ala Leu
1               5                   10                  15

Cys Val Tyr Gly Ala Gly His Leu Glu Gln Pro Gln Ile Ser Ser Thr
            20                  25                  30

Lys Thr Leu Ser Lys Thr Ala Arg Leu Glu Cys Val Val Ser Gly Ile
        35                  40                  45

Thr Ile Ser Ala Thr Ser Val Tyr Trp Tyr Arg Glu Arg Pro Gly Glu
    50                  55                  60

Val Ile Gln Phe Leu Val Ser Ile Ser Tyr Asp Gly Thr Val Arg Lys
65                  70                  75                  80

Glu Ser Gly Ile Pro Ser Gly Lys Phe Glu Val Asp Arg Ile Pro Glu
                85                  90                  95

Thr Ser Thr Ser Thr Leu Thr Ile His Asn Val Glu Lys Gln Asp Ile
            100                 105                 110

Ala Thr Tyr Tyr Cys Ala Leu Trp Glu Glu Leu Gly Lys Lys Ile
        115                 120                 125

Lys Val Phe Gly Pro Gly Thr Lys Leu Ile Ile Thr Asp Lys Gln Leu
    130                 135                 140

Asp Ala Asp Val Ser Pro Lys Pro Thr Ile Phe Leu Pro Ser Ile Ala
145                 150                 155                 160

Glu Thr Lys Leu Gln Lys Ala Gly Thr Tyr Leu Cys Leu Leu Glu Lys
                165                 170                 175

Phe Phe Pro Asp Val Ile Lys Ile His Trp Glu Glu Lys Lys Ser Asn
            180                 185                 190

Thr Ile Leu Gly Ser Gln Glu Gly Asn Thr Met Lys Thr Asn Asp Thr
        195                 200                 205

Tyr Met Lys Phe Ser Trp Leu Thr Val Pro Glu Lys Ser Leu Asp Lys
210                 215                 220

Glu His Arg Cys Ile Val Arg His Glu Asn Asn Lys Asn Gly Val Asp
225                 230                 235                 240

Gln Glu Ile Ile Phe Pro Pro Ile Lys Thr Asp Val Ile Thr Met Asp
                245                 250                 255

Pro Lys Asp Asn Cys Ser Lys Asp Ala Asn Asp Thr Leu Leu Leu Gln
            260                 265                 270

Leu Thr Asn Thr Ser Ala Tyr Tyr Met Tyr Leu Leu Leu Leu Leu Lys
        275                 280                 285

Ser Val Val Tyr Phe Ala Ile Ile Thr Cys Cys Leu Leu Arg Arg Thr
290                 295                 300

Ala Phe Cys Cys Asn Gly Glu Lys Ser
305                 310

<210> SEQ ID NO 9
<211> LENGTH: 867
<212> TYPE: DNA
<213> ORGANISM: Homo sapiens

<400> SEQUENCE: 9
atggagcgga tcagcagcct gatccacctg agcctgttct gggccggagt gatgagcgcc      60
atcgagctgg tgcccgagca ccagaccgtg cccgtgagca tcggcgtgcc cgccaccctg     120
cggtgcagca tgaagggcga ggccatcggc aactactaca tcaactggta cagaaagacc     180
cagggcaaca ccatgacctt catctaccgg gagaaggaca tctacggccc tggcttcaag     240
gacaacttcc agggcgacat cgacatcgcc aagaacctgg ccgtgctgaa gatcctggcc     300
```

```
cccagcgaga gggacgaggg cagctactac tgcgcctgcg acctgctggg ctacaccgac    360
aagctgatct tcggcaaggg cacccgggtg accgtggagc ccagaagcca gccccacacc    420
aagcccagcg tgttcgtgat gaagaacggc accaacgtgg cctgcctggt gaaagagttc    480
taccccaagg acatccggat caacctggtg tccagcaaga agatcaccga gttcgacccc    540
gccatcgtga tcagccccag cggcaagtac aacgccgtga agctgggcaa gtacgaggac    600
agcaacagcg tgacctgcag cgtgcagcac gacaacaaga ccgtgcacag caccgacttc    660
gaggtgaaaa ccgactccac cgaccacgtg aagcccaaag agaccgagaa caccaagcag    720
cccagcaaga ctgccacaa gcccaaggcc atcgtgcaca ccgagaaggt gaacatgatg    780
agcctgaccg tgctgggcct gcggatgctg ttcgccaaga cagtggccgt gaacttcctg    840
ctgaccgcca agctgttctt cctgtga                                       867
```

<210> SEQ ID NO 10
<211> LENGTH: 288
<212> TYPE: PRT
<213> ORGANISM: Homo sapiens

<400> SEQUENCE: 10

```
Met Glu Arg Ile Ser Ser Leu Ile His Leu Ser Leu Phe Trp Ala Gly
1               5                   10                  15

Val Met Ser Ala Ile Glu Leu Val Pro Glu His Gln Thr Val Pro Val
            20                  25                  30

Ser Ile Gly Val Pro Ala Thr Leu Arg Cys Ser Met Lys Gly Glu Ala
        35                  40                  45

Ile Gly Asn Tyr Tyr Ile Asn Trp Tyr Arg Lys Thr Gln Gly Asn Thr
    50                  55                  60

Met Thr Phe Ile Tyr Arg Glu Lys Asp Ile Tyr Gly Pro Gly Phe Lys
65                  70                  75                  80

Asp Asn Phe Gln Gly Asp Ile Asp Ile Ala Lys Asn Leu Ala Val Leu
                85                  90                  95

Lys Ile Leu Ala Pro Ser Glu Arg Asp Glu Gly Ser Tyr Tyr Cys Ala
            100                 105                 110

Cys Asp Leu Leu Gly Tyr Thr Asp Lys Leu Ile Phe Gly Lys Gly Thr
        115                 120                 125

Arg Val Thr Val Glu Pro Arg Ser Gln Pro His Thr Lys Pro Ser Val
    130                 135                 140

Phe Val Met Lys Asn Gly Thr Asn Val Ala Cys Leu Val Lys Glu Phe
145                 150                 155                 160

Tyr Pro Lys Asp Ile Arg Ile Asn Leu Val Ser Ser Lys Lys Ile Thr
                165                 170                 175

Glu Phe Asp Pro Ala Ile Val Ile Ser Pro Ser Gly Lys Tyr Asn Ala
            180                 185                 190

Val Lys Leu Gly Lys Tyr Glu Asp Ser Asn Ser Val Thr Cys Ser Val
        195                 200                 205

Gln His Asp Asn Lys Thr Val His Ser Thr Asp Phe Glu Val Lys Thr
    210                 215                 220

Asp Ser Thr Asp His Val Lys Pro Lys Glu Thr Glu Asn Thr Lys Gln
225                 230                 235                 240

Pro Ser Lys Ser Cys His Lys Pro Lys Ala Ile Val His Thr Glu Lys
                245                 250                 255

Val Asn Met Met Ser Leu Thr Val Leu Gly Leu Arg Met Leu Phe Ala
            260                 265                 270
```

```
Lys Thr Val Ala Val Asn Phe Leu Leu Thr Ala Lys Leu Phe Phe Leu
            275                 280                 285
```

<210> SEQ ID NO 11
<211> LENGTH: 946
<212> TYPE: DNA
<213> ORGANISM: Homo sapiens

<400> SEQUENCE: 11

```
atggtgtccc tgctgcacgc cagcaccctg gccgtgctgg gcgccctgtg cgtgtatggc      60
gccggacacc tggaacagcc ccagatcagc agcaccaaga ccctgagcaa gaccgccagg     120
ctggaatgcg tggtgtccgg catcaccatc agcgccacct ccgtgtactg gtacagagag     180
agacccggcg aggtcatcca gttcctggtg tccatcagct acgacggcac cgtgcggaaa     240
gagagcggca tccccagcgg caagttcgag gtggacagaa tccccgagac cagcaccctcc     300
accctgacca tccacaacgt ggagaagcag gacatcgcca cctactactg cgccctgtgg     360
gagatccagg aactgggcaa gaaaatcaag gtgttcggcc ctggcaccaa gctgatcatc     420
accgacaagc agctggacgc cgacgtgagc cccaagccta ccatcttcct gcccagcatc     480
gccgagacca gctgcagaa ggccggcacc tacctgtgcc tgctggaaaa gttcttcccc     540
gacgtgatca agatccactg gcaggaaaag aagagcaaca ccatcctggg cagccaggaa     600
ggcaatacca tgaaaaccaa cgacacctac atgaagttca gctggctgac cgtgcccgag     660
aagagcctgg acaaagagca cagatgcatc gtccggcacg agaacaacaa gaacggcgtg     720
gaccaggaaa tcatcttccc ccccatcaag accgatgtga tcacaatgga ccccaaggac     780
aactgcagca aggacgccaa cgataccctg ctgctgcagc tgaccaacac cagcgcctac     840
tacatgtatc tcctgctgct gctgaagagc gtggtgtact cgccatcat cacctgctgt     900
ctgctgcggc ggaccgcctt ctgctgcaac ggcgagaaga gctgag               946
```

<210> SEQ ID NO 12
<211> LENGTH: 314
<212> TYPE: PRT
<213> ORGANISM: Homo sapiens

<400> SEQUENCE: 12

```
Met Val Ser Leu Leu His Ala Ser Thr Leu Ala Val Leu Gly Ala Leu
1               5                   10                  15

Cys Val Tyr Gly Ala Gly His Leu Glu Gln Pro Gln Ile Ser Ser Thr
            20                  25                  30

Lys Thr Leu Ser Lys Thr Ala Arg Leu Glu Cys Val Val Ser Gly Ile
        35                  40                  45

Thr Ile Ser Ala Thr Ser Val Tyr Trp Tyr Arg Glu Arg Pro Gly Glu
    50                  55                  60

Val Ile Gln Phe Leu Val Ser Ile Ser Tyr Asp Gly Thr Val Arg Lys
65                  70                  75                  80

Glu Ser Gly Ile Pro Ser Gly Lys Phe Glu Val Asp Arg Ile Pro Glu
                85                  90                  95

Thr Ser Thr Ser Thr Leu Thr Ile His Asn Val Glu Lys Gln Asp Ile
            100                 105                 110

Ala Thr Tyr Tyr Cys Ala Leu Trp Glu Ile Gln Glu Leu Gly Lys Lys
        115                 120                 125

Ile Lys Val Phe Gly Pro Gly Thr Lys Leu Ile Ile Thr Asp Lys Gln
    130                 135                 140

Leu Asp Ala Asp Val Ser Pro Lys Pro Thr Ile Phe Leu Pro Ser Ile
```

```
                145                 150                 155                 160
Ala Glu Thr Lys Leu Gln Lys Ala Gly Thr Tyr Leu Cys Leu Leu Glu
                    165                 170                 175

Lys Phe Phe Pro Asp Val Ile Lys Ile His Trp Glu Lys Lys Ser
                180                 185                 190

Asn Thr Ile Leu Gly Ser Gln Glu Gly Asn Thr Met Lys Thr Asn Asp
                    195                 200                 205

Thr Tyr Met Lys Phe Ser Trp Leu Thr Val Pro Glu Lys Ser Leu Asp
                210                 215                 220

Lys Glu His Arg Cys Ile Val Arg His Glu Asn Asn Lys Asn Gly Val
225                 230                 235                 240

Asp Gln Glu Ile Ile Phe Pro Pro Ile Lys Thr Asp Val Ile Thr Met
                    245                 250                 255

Asp Pro Lys Asp Asn Cys Ser Lys Asp Ala Asn Asp Thr Leu Leu
                260                 265                 270

Gln Leu Thr Asn Thr Ser Ala Tyr Tyr Met Tyr Leu Leu Leu Leu
                    275                 280                 285

Lys Ser Val Val Tyr Phe Ala Ile Ile Thr Cys Cys Leu Leu Arg Arg
290                 295                 300

Thr Ala Phe Cys Cys Asn Gly Glu Lys Ser
305                 310
```

<210> SEQ ID NO 13
<211> LENGTH: 873
<212> TYPE: DNA
<213> ORGANISM: Homo sapiens

<400> SEQUENCE: 13

```
atggagcgga tcagcagcct gatccacctg agcctgttct gggccggagt gatgagcgcc    60
atcgagctgg tgcccgagca ccagaccgtg cccgtgagca tcggcgtgcc cgccaccctg   120
cggtgcagca tgaagggcga ggccatcggc aactactaca tcaactggta cagaaagacc   180
cagggcaaca ccatgacctt catctaccgg gagaaggaca tctacggccc tggcttcaag   240
gacaacttcc agggcgacat cgacatcgcc aagaacctgg ccgtgctgaa gatcctggcc   300
cccagcgaga gggacgaggg cagctactac tgcgcctgcg acgccctgaa gagaaccgac   360
accgacaagc tgatcttcgg caagggcacc cgggtgaccg tggagcccag aagccagccc   420
cacaccaagc ccagcgtgtt cgtgatgaag aacggcacca acgtggcctg cctggtgaaa   480
gagttctacc ccaaggacat ccggatcaac ctggtgtcca gcaagaagat caccgagttc   540
gaccccgcca tcgtgatcag ccccagcggc aagtacaacg ccgtgaagct gggcaagtac   600
gaggacagca cagcgtgac ctgcagcgtg cagcacgaca acaagaccgt gcacagcacc   660
gacttcgagg tgaaaaccga ctccaccgac cacgtgaagc ccaagagac cgagaacacc   720
aagcagccca gcaagagctg ccacaagccc aaggccatcg tgcacaccga aaggtgaac   780
atgatgagcc tgaccgtgct gggcctgcgg atgctgttcg ccaagacagt ggccgtgaac   840
ttcctgctga ccgccaagct gttcttcctg tga                                873
```

<210> SEQ ID NO 14
<211> LENGTH: 290
<212> TYPE: PRT
<213> ORGANISM: Homo sapiens

<400> SEQUENCE: 14

Met Glu Arg Ile Ser Ser Leu Ile His Leu Ser Leu Phe Trp Ala Gly

```
1               5                   10                  15
Val Met Ser Ala Ile Glu Leu Val Pro Glu His Gln Thr Val Pro Val
                20                  25                  30

Ser Ile Gly Val Pro Ala Thr Leu Arg Cys Ser Met Lys Gly Glu Ala
                35                  40                  45

Ile Gly Asn Tyr Tyr Ile Asn Trp Tyr Arg Lys Thr Gln Gly Asn Thr
            50                  55                  60

Met Thr Phe Ile Tyr Arg Glu Lys Asp Ile Tyr Gly Pro Gly Phe Lys
65                  70                  75                  80

Asp Asn Phe Gln Gly Asp Ile Asp Ile Ala Lys Asn Leu Ala Val Leu
                85                  90                  95

Lys Ile Leu Ala Pro Ser Glu Arg Asp Glu Gly Ser Tyr Tyr Cys Ala
                100                 105                 110

Cys Asp Ala Leu Lys Arg Thr Asp Thr Asp Lys Leu Ile Phe Gly Lys
                115                 120                 125

Gly Thr Arg Val Thr Val Glu Pro Arg Ser Gln Pro His Thr Lys Pro
            130                 135                 140

Ser Val Phe Val Met Lys Asn Gly Thr Asn Val Ala Cys Leu Val Lys
145                 150                 155                 160

Glu Phe Tyr Pro Lys Asp Ile Arg Ile Asn Leu Val Ser Ser Lys Lys
                165                 170                 175

Ile Thr Glu Phe Asp Pro Ala Ile Val Ile Ser Pro Ser Gly Lys Tyr
                180                 185                 190

Asn Ala Val Lys Leu Gly Lys Tyr Glu Asp Ser Asn Ser Val Thr Cys
                195                 200                 205

Ser Val Gln His Asp Asn Lys Thr Val His Ser Thr Asp Phe Glu Val
                210                 215                 220

Lys Thr Asp Ser Thr Asp His Val Lys Pro Lys Glu Thr Glu Asn Thr
225                 230                 235                 240

Lys Gln Pro Ser Lys Ser Cys His Lys Pro Lys Ala Ile Val His Thr
                245                 250                 255

Glu Lys Val Asn Met Met Ser Leu Thr Val Leu Gly Leu Arg Met Leu
                260                 265                 270

Phe Ala Lys Thr Val Ala Val Asn Phe Leu Leu Thr Ala Lys Leu Phe
                275                 280                 285

Phe Leu
    290

<210> SEQ ID NO 15
<211> LENGTH: 6
<212> TYPE: PRT
<213> ORGANISM: Homo Sapiens

<400> SEQUENCE: 15

Ala Leu Lys Arg Thr Asp
1               5

<210> SEQ ID NO 16
<211> LENGTH: 14
<212> TYPE: PRT
<213> ORGANISM: Homo Sapiens
```

```
<400> SEQUENCE: 16

Ala Leu Trp Glu Ile Gln Glu Leu Gly Lys Lys Ile Lys Val
1               5                   10

<210> SEQ ID NO 17
<211> LENGTH: 14
<212> TYPE: PRT
<213> ORGANISM: Homo Sapiens

<400> SEQUENCE: 17

Ala Cys Asp Ala Leu Lys Arg Thr Asp Thr Asp Lys Leu Ile
1               5                   10

<210> SEQ ID NO 18
<211> LENGTH: 12
<212> TYPE: PRT
<213> ORGANISM: Homo Sapiens

<400> SEQUENCE: 18

Ala Cys Asp Leu Leu Gly Tyr Thr Asp Lys Leu Ile
1               5                   10

<210> SEQ ID NO 19
<211> LENGTH: 8
<212> TYPE: PRT
<213> ORGANISM: Homo Sapiens

<400> SEQUENCE: 19

Thr Leu Gly Met Gly Gly Glu Tyr
1               5

<210> SEQ ID NO 20
<211> LENGTH: 2
<212> TYPE: PRT
<213> ORGANISM: homo sapiens

<400> SEQUENCE: 20

Ile Gln
1

<210> SEQ ID NO 21
<211> LENGTH: 3
<212> TYPE: PRT
<213> ORGANISM: homo sapiens

<400> SEQUENCE: 21

Ala Gln Gln
1

<210> SEQ ID NO 22
<211> LENGTH: 4
<212> TYPE: PRT
<213> ORGANISM: homo sapiens

<400> SEQUENCE: 22

Leu Leu Gly Tyr
1
```

GAMMA 9 DELTA 2 T CELL RECEPTORS

CROSS-REFERENCE TO RELATED APPLICATIONS

This application is a U.S. National Stage filing under 35 U.S.C. §371 of International Application No. PCT/NL2013/050235, filed Mar. 28, 2013, which in turn claims priority to U.S. Provisional Patent Application No. 61/616,440, filed Mar. 28, 2012 and also to U.S. Provisional Patent Application No. 61/703,788, filed Sep. 21, 2012, the entire contents of which are incorporated by reference herein.

FIELD OF THE INVENTION

The invention is in the field of medicine. It relates to immunology and to cell therapy for the treatment of cancer. The invention further relates to the methods for identification of T cell receptors, in particular T cell receptors that may mediate anti-tumour responses. The invention further relates to specific T-cell receptors that mediate anti-tumour responses and uses thereof, in the treatment of cancer.

BACKGROUND ART

So far, allogeneic stem cell transplantation (allo-SCT) is the only well established and proven curative cellular therapy for patients suffering from cancer. This is demonstrated by the observation that long term remissions can be in particular achieved with allo-SCT in patients with "poor-risk" leukaemia. However, cure comes at a price of severe toxicity, resulting in an overall mortality of approximately 30% of treated patients. This hampers broad clinical implementation as in particular patients with low risk cancers might have a good overall survival not justifying such aggressive therapies. The ultimate goal remains therefore the development of a non-aggressive transplantation method. This means the generation of cellular products equipped with molecular features that allow selective targeting of the cancer cell while preserving healthy tissues. This would allow a curative treatment to a large number of patients with medical need, irrespective of age.

To engineer a transplant, which may be allogeneic or autologous, to facilitate the rapid generation of e.g. tumour-reactive αβT-cells, it has been proposed to reprogram αβT-cells with genes encoding for a tumour-specific αβT-cell receptor (TCR) or a chimeric antigen receptor. Several of such receptors are already being used to redirect αβT-cells in phase I clinical trials. However, reprogramming αβT-cells with defined αβTCRs is substantially hampered by their restriction to HLA types, limiting thereby the number of patients that can be treated with one αβ-TCR. In addition, pairing of introduced αβTCR chains with endogenous αβTCR chains can induce life-threatening auto-reactivity.

It has been proposed to mediate a selective anti-tumour-reactivity with a high-affinity TCR using the ability of γ9δ2T-cells to mediate anti-tumour-reactivity while ignoring healthy-environment (Fisch et al., 1990, Science 250, 1269-1273). Isolated γ9δ2T-cells may efficiently kill tumour-cells of haematological malignancies and solid tumours (Kabelitz et al., 2007, Cancer Res. 67, 5-8). However, the function and proliferation capacity of γ9δ2T-cells is frequently heavily impaired in cancer patients making autologous γ9δ2T-cells less attractive for immune interventions.

It has been proposed to transfer a defined γ9δ2TCR into αβT-cells, which mediates a tumour-specific proliferation of αβT-cells and redirects both effector CD8+ and helper CD4+ αβT-cell subsets against a broad panel of tumour-cell-lines while normal cells in vitro and in vivo may be ignored (Marcu-Malina et al., 2011, Blood 118, 50-59). However, little knowledge is available about how γ9δ2TCRs mediate different activity against tumour cells and what strategy needs to be used to isolate γ9δ2TCRs with high activity against cancer cells.

Hence, there is need in the art to provide for γ9δ2TCRs with high activity against cancer cells and there is a need in the art to provide for improved methods for selecting such highly active γ9δ2TCRs.

SUMMARY OF THE INVENTION

The current invention provides methods to identify γ9δ2T-cell receptors (γ9δ2TCR) that mediate anti-tumour responses. As said, little knowledge is available about the molecular requirements of a γ9δ2TCRs to mediate anti-tumour reactivity. Especially the contribution of the variability within the complementary determining regions (CDRs) of the γ9δ2TCR for mediating anti-tumour responses was regarded as negligible in the prior art. Surprisingly, it was now found that the CDR3 regions of the γ9T-cell receptor chain (γ9TCR chain) and the δ2T-cell receptor chain (δ2TCR chain) are of importance. Based on these findings, combinatorial-γδTCR-chain-exchange (CTE) is proposed as an efficient method for identifying γ9δ2TCRs that mediate anti-tumour responses. In the methods of the invention, the CDR3 regions of the γ9T-cell receptor chain and the δ2T-cell receptor chain are randomly modified and combined to form a novel γ9δ2TCR. The newly designed γ9δ2TCR is provided and preferably integrated into T-cells, which subsequently express a γ9δ2TCR at the cell surface. Accordingly the anti-tumour response of the CTE-engineered T-cells is determined. In this way multiple combinations can be tested, and for each combination the anti-tumour response can be determined. After determining the anti-tumour response, γ9δ2T-cell receptors that mediate highly active anti-tumour responses can be identified. Using the method of the invention, such as described in the examples, already several responsive γ9δ2TCRs were identified that mediate increased anti-tumour responses compared to the reference γ9δ2TCR G115wt. Hence, the invention further provides for γ9δ2TCRs, or fragments thereof, that may be used e.g. in diagnostics or the treatment of cancer. The invention further provides for nucleic acid sequences, genetic constructs and retroviral vectors that can be used to express the γ9δ2TCRs in cells, preferably T cells, according to the invention.

FIGURES

FIGS. 1A-F: Anti-tumour reactivity mediated by γ9δ2TCRs.
Peripheral blood T-cells were virally transduced with indicated wildtype γ9δ2TCRs or CTE-engineered γ9δ2TCRs and tested against Daudi (A, C) in a $^{51}$Cr-release assay (E:T 3:1). Specific lysis is indicated as fold change $^{51}$Cr-release measured in the supernatant after 5 h. Fold change was calculated when compared to reactivity of γ9-G115$_{wt}$/δ2-G115$_{wt}$ engineered T-cells. (B, D) in an IFNγ ELISA in the presence of indicated amounts of pamidronate or (E) different E:T ratios. (F) Percentages of cell-cell conjugates of Daudi and T-cells engineered with indicated γ9δ2TCR were determined by flow cytometry. Data represent the mean±SD. *p<0.05, p<0.01, *p<0.001 by 1-way ANOVA.

FIGS. 2A-D: γ9δ2TCR expression and functional avidity of transduced T-cells expressing single alanine mutated δ2 chain of clone G115.

Peripheral blood T-cells were virally transduced with indicated γ9 and δ2 TCR chains and (A) analyzed by flow cytometry using a δ2-chain specific antibody. Shown is the fold change in mean fluorescent intensity (MFI) in comparison to wildtype control expressing δ2-G115$_{wt}$. (C) Lytic activity of transductants was tested in a $^{51}$Cr-release assay against the tumour target Daudi (E:T 10:1). Specific lysis is indicated as fold change $^{51}$Cr-release measured in the supernatant after 5 h. Fold change was calculated as compared to reactivity of unmutated wildtype (δ2-G115$_{wt}$). Arrows indicate mutations in δ2-G115 that impaired receptor expression (dashed arrows) or functional avidity (solid arrows). (B, D) Crystal structure of γ9δ2TCR G115 indicating relevant amino acids (arrows).

FIGS. 3A-F: γ9δ2TCR expression and functional avidity of transduced T-cells expressing γ9δ2TCR G115 with δ2-CDR3 length mutations.

(A) γ9δ2TCR expression of indicated transductants was analyzed by flow cytometry using a γδTCR-pan antibody. Shown is the fold change in mean fluorescent intensity (MFI) in comparison to wildtype control expressing δ2-G115$_{wt}$. (B) IFNγ secretion of δ2-G115$_{LM}$ transduced T-cells against the tumour target Daudi (E:T 1:1) was measured by ELISA after 24 h incubation in the presence of 100 μM pamidronate. Shown is the fold change in IFNγ production when compared to reactivity of transductants expressing wt δ2-G115$_{wt}$. (C) Transductants expressing δ2-G115$_{LM0,1,4,12}$ were tested in a titration assay against the tumour target Daudi with increasing amounts of pamidronate as indicated. IFNγ production was measured after 24 h by ELISA. (D) Generated δ2-G115$_{LMs}$ were matched in a BLAST search with γ9δ2TCRs described in the IMGT database. Shown is the number of citations compared to δ2-G115$_{LM}$ of similar δCDR3 length. (E) Transductants with δ2-G115$_{LM2,4,6}$ were compared side-by-side to transductants expressing individual γ9δ2TCRs of the same δCDR3 length. IFNγ secretion of transduced T-cells against the tumour target Daudi (E:T 1:1) was measured by ELISA after 24 h in the presence of 100 μM pamidronate. Shown is the fold change in IFNγ production compared to reactivity of transductants expressing wt δ2-G115$_{wt}$. Data represent the mean±SD. p<0.01, p<0.001 by 1-way ANOVA. (F) Crystal structure of γ9δ2TCR G115; the region that was used for alanine stretches within δCDR3 is shown in white, residual δCDR3 in green, δ chain in blue, γ chain in brown.

Figure 4:
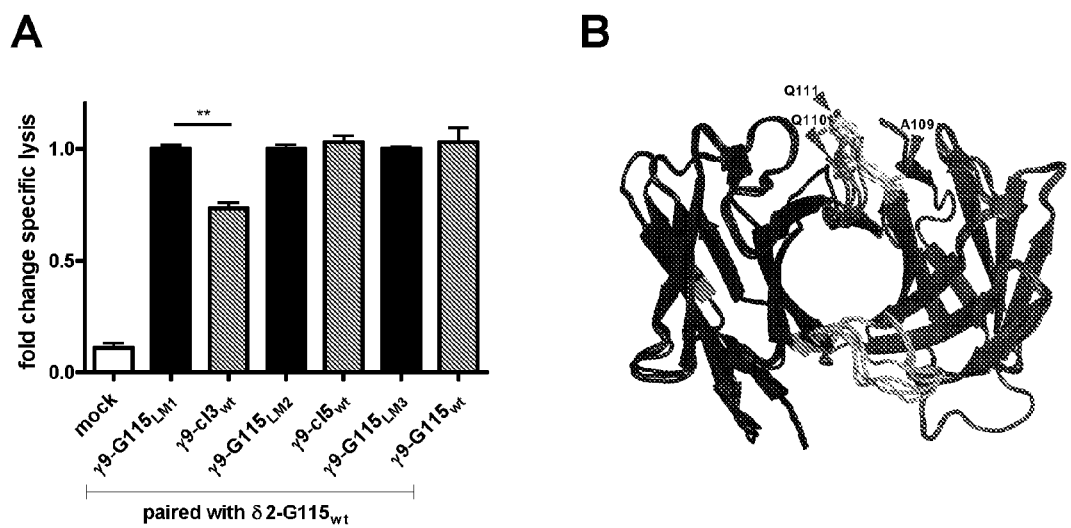

FIGS. 4A-B: Functional avidity of transduced T-cells expressing γ9δ2TCR G115 with γ9-CDR3 length mutations.

(A) Peripheral blood T-cells were virally transduced with indicated γ9 and δ2 TCR chains. Lytic activity of transductants was compared side-by-side to T-cells expressing individual γ9δ2TCRs of the same γ9CDR3 length. Specific lysis is indicated as fold change $^{51}$Cr-release measured in the supernatant after 5 h. Data represent the mean±SD. **p<0.01 by 1-way ANOVA. (B) Crystal structure of γ9δ2TCR G115 indicating γ9CDR3 in gray including amino acids γ9-G115$_{A109}$, γ9-G115$_{Q110}$ and γ9-G115$_{Q111}$ (red arrows), δCDR3 is shown in green; δ chain in blue; γ chain in brown.

Figure 5:
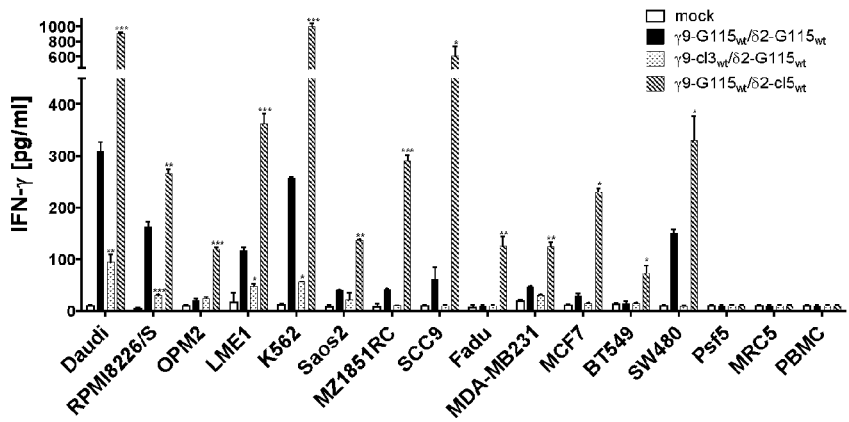
Figure 5:
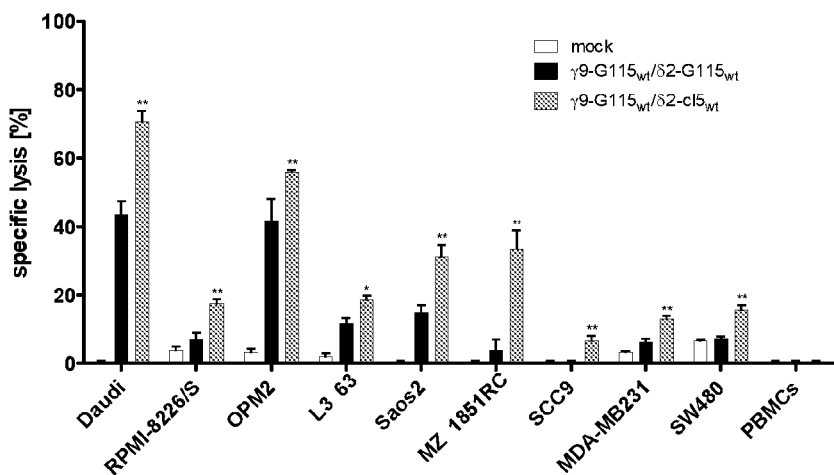
Figure 5:
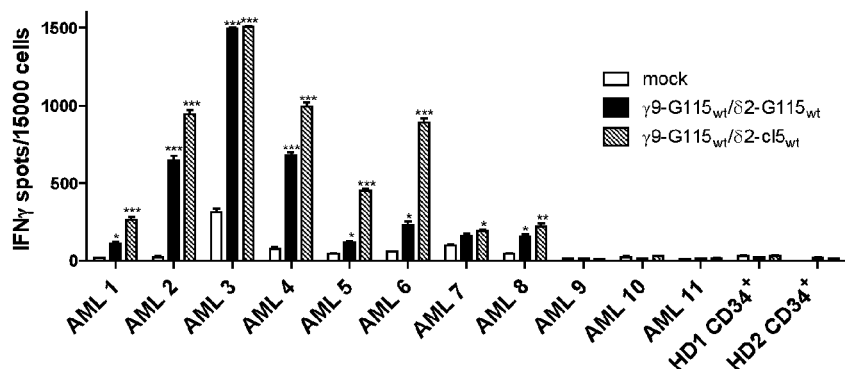

FIGS. 5A-C: Anti-tumour reactivity of T-cells transduced with CTE-engineered γ9δ2TCRs in vitro.

Peripheral blood T-cells were virally transduced with indicated γ9δ2TCRs and tested against indicated tumour cell lines and healthy control tissue. (A) Transductants were incubated with target cells (E:T 1:1) in the presence of 10 μM pamidronate. IFNγ production was measured after 24 h by ELISA. Data represent the mean±SD. *p<0.05, p<0.01, *p<0.001 by 1-way ANOVA. (B) Transductants were incubated with indicated tumour targets loaded with $^{51}$Cr (E:T 10:1). Percentage of specific lysis was determined by $^{51}$Cr-release measured in the supernatant after 5 h. (C) CTE-engineered T-cells were tested against primary AML blasts and healthy progenitor cells in an IFNγ ELISpot assay (E:T 3:1) in the presence of 10 μM pamidronate. Data represent the mean±SD. *p<0.05, p<0.01, *p<0.001 by 1-way ANOVA.

Figure 6:
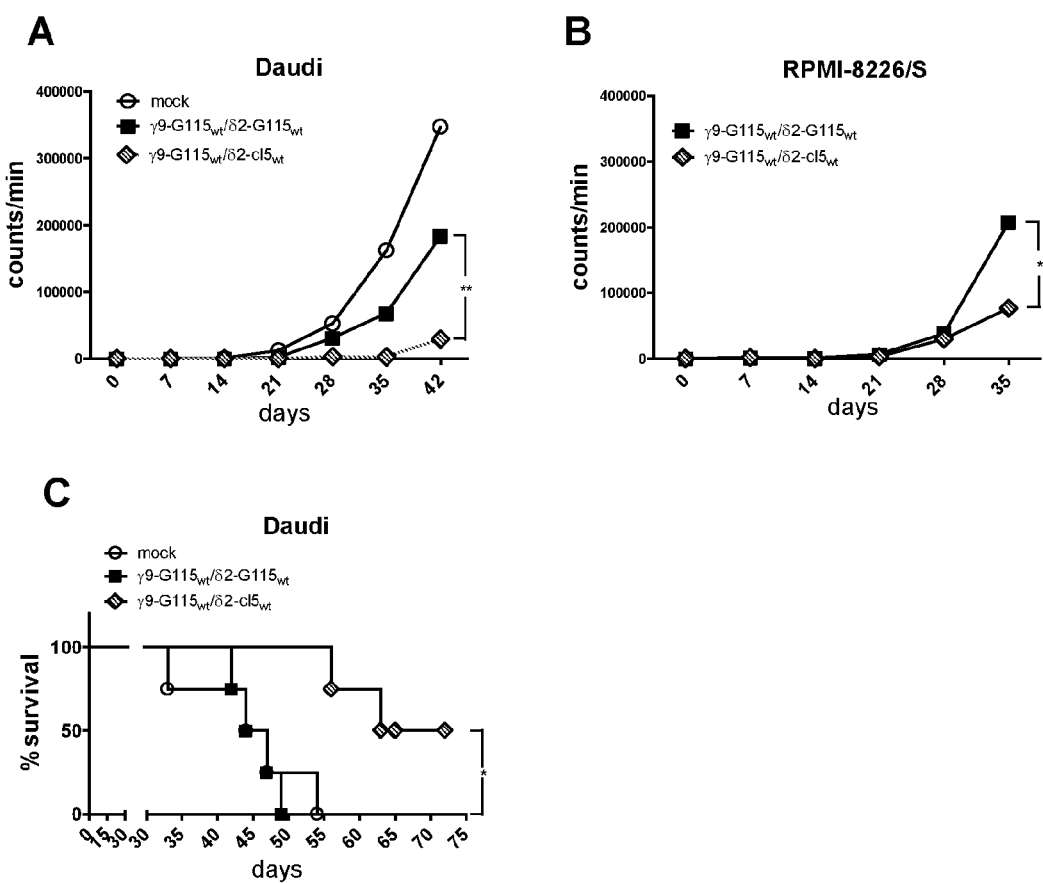
Figure 7:
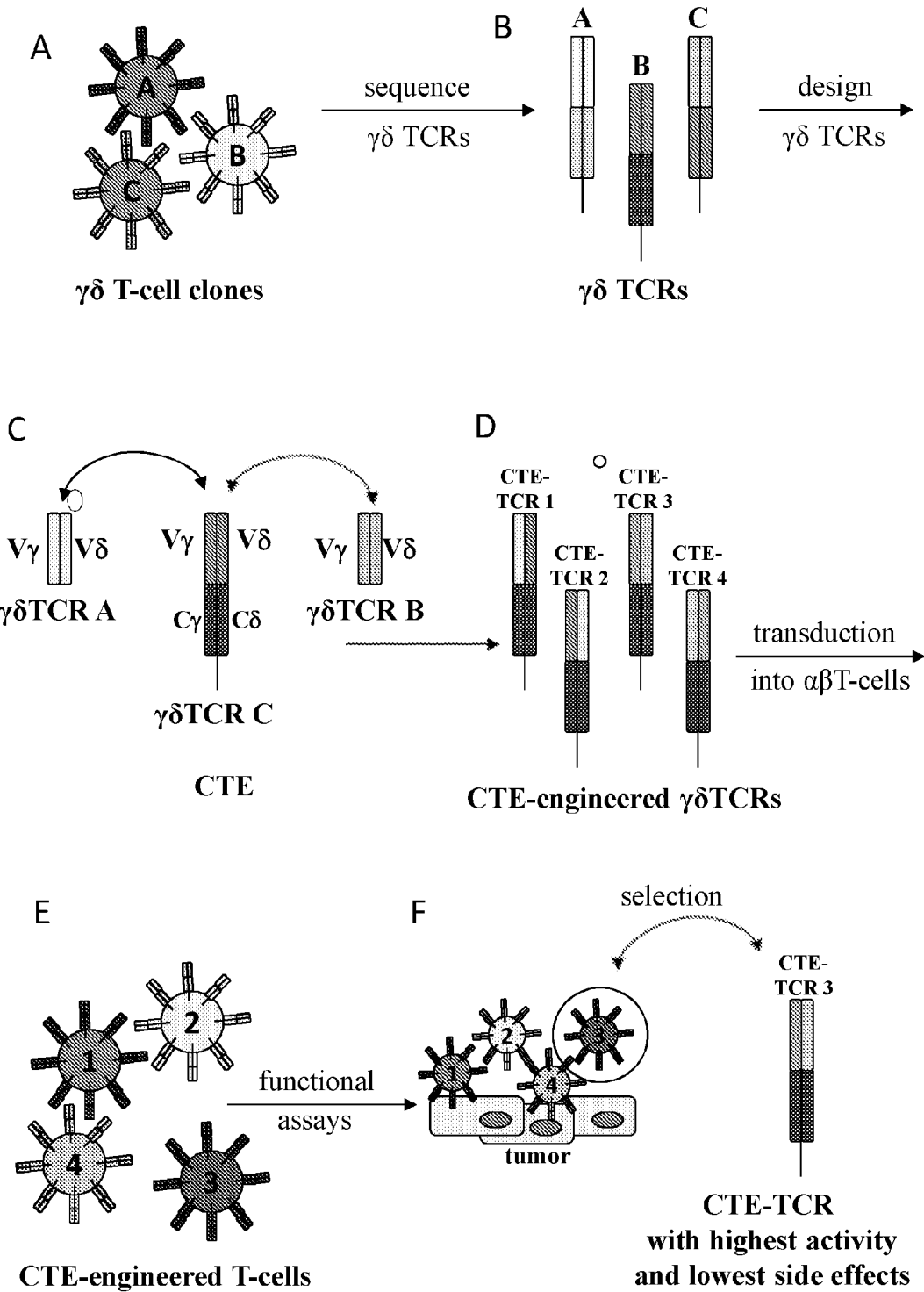

FIGS. 6A-C: Anti-tumour reactivity of T-cells transduced with CTE-engineered γ9δ2TCRs in vivo.

The functional avidity of T-cells expressing CTE-γ9δ2TCR γ9-G115$_{wt}$/δ2-cl5$_{wt}$ or control γ9δ2TCR (γ9-G115$_{wt}$/δ2-G115$_{wt}$) was studied in Rag2$^{-/-}$γc$^{-/-}$ double knockout mice (4-7 mice per group). After total body irradiation (2Gy) on day 0, mice were intravenously injected with 0.5×10$^6$ Daudi-luciferase or 5×10$^6$ RPMI8226/S-luciferase cells and 10$^7$ CTE-γ9δ2TCR transduced T-cells at day 1. Additionally, 6×10$^5$ IU IL2 in IFA and pamidronate (10 mg/kg body weight) were injected at day 1 and every 3 weeks until the end of the experiment. (A,B) Tumour outgrowth was assessed in vivo by bioluminescence imaging (BLI) by measuring the entire area of mice on both sides. Data represent the mean of all animals measured (Daudi: n=4, RPMI8226/S: n=7). *p<0.05, **p<0.01 by 1-way ANOVA (Daudi: day 42; RPMI8226/S: day 35). (C) Overall survival of treated Daudi mice was monitored for 72 days. *p<0.05, **p<0.01 by logrank (Mantel-Cox) test.

FIGS. 7A-F. Combinatorial-γδTCR-chain-exchange (CTE)

Individual γ9δ2T-cell clones are isolated (A) and the sequence of the γ9TCR and δ2TCR chain is determined (B). By Combinatorial-γδTCR-chain exchange novel γ9δ2TCRs are designed whereby γ9- and δ2CDR3 regions are randomly modified (e.g. via amino acid substitutions, deletions and/or insertions and/or shortening or stretching of the CDR3 length) (C) and newly combined (D). Subsequently novel γ9δ2TCRs are introduced into cells, preferably T-cells such as αβT-cells (e.g. via transduction using a retroviral vector encoding the γ9TCR and δ2TCR chains) and CTE-engineered T-cells are provided (E). Finally, CTE-engineered T-cells are tested against tumour cells in functional assays to determine γ9δ2TCRs that mediate high anti-tumour responses. Hence, γ9δ2TCRs with e.g. the highest anti-tumour response and/or lowest side effects can be selected (F).

DEFINITIONS

In the following description and examples a number of terms are used. In order to provide a clear and consistent understanding of the specifications and claims, including the scope to be given to such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

Methods of carrying out the conventional techniques used in methods of the invention will be evident to the skilled worker. The practice of conventional techniques in molecular biology, biochemistry, computational chemistry, cell culture, recombinant DNA, bioinformatics, genomics, sequencing and related fields are well-known to those of skill in the art and are discussed, for example, in the following literature references: Sambrook et al., Molecular Cloning. A Laboratory Manual, 2nd Edition, Cold Spring Harbor Laboratory Press, Cold Spring Harbor, N.Y., 1989; Ausubel et al., Current Protocols in Molecular Biology, John Wiley & Sons, New York, 1987 and periodic updates; and the series Methods in Enzymology, Academic Press, San Diego.

In this document and in its claims, the verb "to comprise" and its conjugations is used in its non-limiting sense to mean that items following the word are included, but items not specifically mentioned are not excluded. It encompasses the verbs "consisting essentially of" as well as "consisting of".

As used herein, the singular forms "a," "an" and "the" include plural referents unless the context clearly dictates otherwise. For example, a method for isolating "a" DNA molecule, as used above, includes isolating a plurality of molecules (e.g. 10's, 100's, 1000's, 10's of thousands, 100's of thousands, millions, or more molecules).

Aligning and alignment: With the term "aligning" and "alignment" is meant the comparison of two or more nucleotide sequences based on the presence of short or long stretches of identical or similar nucleotides. Several methods for alignment of nucleotide sequences are known in the art, as will be further explained below. With the term "aligning" and "alignment" is also meant the comparison of two or more amino acid sequences based on the presence of short or long stretches of identical or similar amino acids. Several methods for alignment of amino acid sequences are known in the art, as will be further explained below.

"Expression of a gene" refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment) or which is active itself (e.g. in posttranscriptional gene silencing or RNAi). An active protein in certain embodiments refers to a protein being constitutively active. The coding sequence is preferably in sense-orientation and encodes a desired, biologically active protein or peptide, or an active peptide fragment.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous and, where necessary to join two or more protein encoding regions, contiguous and in reading frame.

The term "genetic construct" means a DNA sequence comprising a region (transcribed region), which is transcribed into an RNA molecule (e.g. an mRNA) in a cell, operably linked to suitable regulatory regions (e.g. a promoter). A genetic construct may thus comprise several operably linked sequences, such as a promoter, a 5' leader sequence comprising e.g. sequences involved in translation initiation, a (protein) encoding region, splice donor and acceptor sites, intronic and exonic sequences, and a 3' non-translated sequence (also known as 3' untranslated sequence or 3'UTR) comprising e.g. transcription termination sequence sites.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER; Gribskov, M. and Devereux, J., eds., M Stockton Press, New York, 1991). While a number of methods exist to measure identity between two polynucleotide or polypeptide sequences, the term "identity" is well known to skilled artisans (Carillo, H., and Lipton, D., SIAM J. Applied Math (1988) 48:1073). Methods commonly employed to determine identity or similarity between two sequences include, but are not limited to, those disclosed in GUIDE TO HUGE COMPUTERS, Martin J. Bishop, ed., Academic Press, San Diego, 1994, and Carillo, H., and Lipton, D., SIAM J. Applied Math (1988) 48:1073. Methods to determine identity and similarity are codified in computer programs. Preferred computer program methods to determine identity and similarity between two sequences include, but are not limited to, GCS program package (Devereux, J., et al., Nucleic Acids Research (1984) 12(1):387), BLASTP, BLASTN, FASTA (Atschul, S. F. et al., J. Molec. Biol. (1990) 215:403).

As an illustration, by a polynucleotide having a nucleotide sequence having at least, for example, 95% "identity" to a reference nucleotide sequence encoding a polypeptide of a certain sequence it is intended that the nucleotide sequence of the polynucleotide is identical to the reference sequence except that the polynucleotide sequence may include up to five point mutations per each 100 nucleotides of the reference polypeptide sequence. Hence, the percentage of identity of a nucleotide sequence to a reference nucleotide sequence is to be calculated over the full length of the reference nucleotide sequence. In other words, to obtain a polynucleotide having a nucleotide sequence at least 95% identical to a reference nucleotide sequence, up to 5% of the nucleotides in the reference sequence may be deleted and/or substituted with another nucleotide, and/or a number of nucleotides up to 5% of the total nucleotides in the reference sequence may be inserted into the reference sequence. These mutations of the reference sequence may occur at the 5' or 3' terminal positions of the reference nucleotide sequence, or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO: 1 or 2 is intended that the amino acid sequence of the polypeptide is identical to the reference sequence except that the polypeptide sequence may include up to five amino acid alterations per each 100 amino acids of the reference amino acid of SEQ ID NO: 1 or 2. Hence, the percentage of identity of an amino acid sequence to a reference amino acid sequence is to be calculated over the full length of the reference amino acid sequence. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

A "nucleic acid" or "nucleic acid sequence" according to the present invention may include any polymer or oligomer of pyrimidine and purine bases, preferably cytosine, thymine, and uracil, and adenine and guanine, respectively (See Albert L. Lehninger, *Principles of Biochemistry*, at 793-800 (Worth Pub. 1982), which is herein incorporated by reference in its entirety for all purposes). The present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogenous or homogenous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

As used herein, the term "promoter" refers to a nucleic acid sequence that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. Optionally the term "promoter" includes herein also the 5' UTR region (5' Untranslated Region) (e.g. the promoter may herein include one or more parts upstream (5') of the translation initiation codon of a gene, as this region may have a role in regulating transcription and/or translation). A "constitutive" promoter is a promoter that is active in most tissues under most physiological and developmental conditions. An "inducible" promoter is a promoter that is physiologically (e.g. by external application of certain compounds) or developmentally regulated. A "tissue specific" promoter is only active in specific types of tissues or cells. A "promoter active in a particular cell type, e.g. in T cells" refers to the general capability of the promoter to drive transcription within such a cell type. It does not make any implications about the spatio-temporal activity of the promoter.

The terms "amino acid sequence" or "protein" or "peptide" refer to molecules consisting of a chain of amino acids, without reference to a specific mode of action, size, 3 dimensional structure or origin. A "fragment" or "portion" of thereof may thus still be referred to as an "amino acid sequence" or "protein" or "peptide". An "isolated amino acid sequence" is used to refer to an amino acid sequence which is no longer in its natural environment, for example in vitro or in a recombinant bacterial or human host cell.

"Engineered cells" refers herein to cells having been engineered, e.g. by the introduction of an exogenous nucleic acid sequence or specific alteration of an endogenous gene sequence. Such a cell has been genetically modified for example by the introduction of for example one or more mutations, insertions and/or deletions in the endogenous gene and/or insertion of a genetic construct in the genome.

An engineered cell may refer to a cell in isolation or in culture. Engineered cells may be "transduced cells" wherein the cells have been infected with e.g. a modified virus, for example, a retrovirus may be used, such as described in the examples, but other suitable viruses may also be contemplated such as lentiviruses. Non-viral methods may also be used, such as transfections. Engineered cells may thus also be "stably transfected cells" or "transiently transfected cells". Transfection refers to non-viral methods to transfer DNA (or RNA) to cells such that a gene is expressed. Transfection methods are widely known in the art, such as calciumphosphate transfection, PEG transfection, and liposomal or lipoplex transfection of nucleic acids. Such a transfection may be transient, but may also be a stable transfection wherein cells can be selected that have the gene construct integrated in their genome.

"Randomly modifying" includes generating random sequences, and also includes selecting δ2-CDR3 encoding regions and/or γ9-CDR-3 encoding regions that are occurring in nature and can be derived from γ9δ2T cell receptor sequences derived from subjects, e.g. from humans, such as described in the example section wherein such γ9-CDR3 and δ2-CDR3 sequences were selected from a database. Generating random sequences includes modifying one or several amino acids in a starting γ9-CDR-3 and δ2-CDR3 sequence, up to the point wherein all the amino acids from the starting sequences may be modified. Modifying amino acid sequences may be done by changing nucleotide sequences of a codon such that the amino acid encoded by that codon is altered.

The term "corresponding to" with regard to amino acid sequences means that when one sequence is aligned with a reference sequence which comprises a corresponding sequence, for example amino acid residues 50-70, the amino acids aligning with the example amino acid residues 50-70 are the amino acid residues of the one sequence that are corresponding. An example of an alignment in which corresponding amino acids are aligned from γ9-CDR3 and δ2-CDR3 regions is depicted in table 3.

The term "selectable marker" is a term familiar to one of ordinary skill in the art and is used herein to describe any genetic entity which, when expressed, can be used to select for a cell or cells containing the selectable marker. Selectable marker gene products confer for example antibiotic resistance, or another selectable trait or a nutritional requirement. Selectable markers such as well-known in the art include green fluorescent protein (GFP), eGFP, luciferase, GUS and the like.

DETAILED DESCRIPTION OF THE INVENTION

In a first aspect, the invention relates to a method for identifying γ9δ2T-cell receptors that mediate anti-tumour responses comprising the steps of:
  a) providing T-cells;
  b) providing a nucleic acid sequence encoding a γ9-T-cell receptor chain comprising a γ9-CDR3 encoding region, wherein the γ9-CDR3 encoding region is randomly modified, and a nucleic acid sequence encoding a δ2-T-cell receptor chain comprising a δ2-CDR3 encoding region, wherein the δ2-CDR3 encoding region is randomly modified;
  c) introducing the nucleic acid sequences of step b) into the T-cells to provide for an engineered T-cell with a γ9δ2T-cell receptor comprising the γ9-T-cell receptor chain of step b) and the δ2-T-cell receptor chain of step b);

d) optionally, repeating steps b) and c);

e) determining the anti-tumour response of the engineered T-cells provided in steps c) and d);

f) identifying the γ9δ2T-cell receptors of the engineered T-cells that mediate anti-tumour responses.

T cells, or T lymphocytes, belong to a group of white blood cells named lymphocytes, which play a role in cell-mediated immunity. T cells originate from hematopoietic stem cells in the bone marrow, mature in the thymus (that is where the T is derived from), and gain their full function in peripheral lymphoid tissues. During T-cell development, CD4$^-$CD8$^-$ T-cells (negative for both the CD4 and CD8 co-receptor) are committed either to an αβ or γδ fate as a result of an initial β or δ TCR gene rearrangement. Cells that undergo early β chain rearrangement express a pre-TCR structure composed of a complete β chain and a pre-TCRα chain on the cell surface. Such cells switch to a CD4$^+$CD8$^+$ state, rearrange the TCRα chain locus, and express a mature αβTCR on the surface. CD4$^-$CD8$^-$ T cells that successfully complete the γ gene rearrangement before the β gene rearrangement express a functional γδTCR and remain CD4$^-$CD8$^-$. (Claudio Tripodo et al. Gamm delta T cell lymphomas Nature Reviews Clinical Oncology 6, 707-717 (December 2009). The T cell receptor associates with the CD3 protein complex. Mature T cells, i.e. expressing a αβTCR or a γδTCR, express the T cell receptor complex on the cell surface. The γδT-cells, which constitute about 1-5% of the total population of T cells, can be divided in further subpopulations. A subpopulation of γδT-cells constitutes γ9δ2T-cells, which express a γ9δ2TCR. Within the extracellular domain of a T cell receptor three complementarity determining regions (CDR1, CDR2, CDR3) are located. These regions are in general the most variable domains and contribute significantly to the diversity among TCRs. CDR regions are composed during the development of a T-cell where so-called Variable-(V), Diverse-(D), and Joining-(J)-gene segments are randomly combined to generate diverse TCRs.

αβT cells may be defined with respect of function as T lymphocytes that express an αβTCR, which recognises peptides bound to MHC molecules (major histocompatibility complex), which are expressed on the surface of various cells. MHCs present peptides derived from the proteins of a cell. When for example a cell is infected with a virus, the MHC will present viral peptides, and the interaction between the αβTCR and the MHC-complex activates specific types of T-cells which initiate and immune responses to eliminate the infected cell. Hence, αβT cells may be functionally defined as being cells capable of recognizing peptides bound to MHC molecules. αβT cells may be selected from peripheral blood for example via the CD3 antigen as described below and in the examples, as the large majority of T cells have the αβTCR. αβT cells may also be selected with an antibody specific for the αβTCR, such as described below. From such selected cells, the nucleic acid (or amino acid) sequence corresponding to the αT-cell receptor chain and the βT-cell receptor chain may be determined. Hence, αβT-cells may also be defined as being cells comprising a nucleic acid (or amino acid) sequence corresponding to the αT-cell receptor chain and/or the βT-cell receptor chain.

γ9δ2T-cells may be functionally defined in that they are specifically and rapidly activated by a set of non-peptidic phosphorylated isoprenoid precursors, collectively named phosphoantigens. Phosphoantigens are produced by virtually all living cells. The most common phosphoantigen found in animal and human cells (including cancer cells) is isopentenyl pyrophosphate (IPP) and its isomer dimethylallyl pyrophosphate (DMAPP). Activation of γ9δ2T-cells comprises clonal expansion, cytoxic activity and expression of cytokine. γ9δ2T-cells are also defined by expression of the γ9δ2T-cell receptor. For example, cells may be selected using an antibody specific for the γ9δ2T-cell receptor such as described below. From such selected cells, the nucleic acid (or amino acid sequence) sequence corresponding to the γ9T-cell receptor chain and/or the δ2T-cell receptor chain may be determined. Hence, γ9δ2T-cells may also be defined as being cells comprising a nucleic acid (or amino acid) sequence corresponding to a γ9T-cell receptor chain and/or a δ2T-cell receptor chain.

The person skilled in the art is well capable of selecting and/or identifying cell populations characterized by expression of an antigen or receptor on the surface of the cell such as described throughout herein. It is understood that with regard to expression on the surface of cells, such as CD3, CD4, CD8, αβTCR, γδTCR and γ9δ2TCR, this is typically done in a population of cells of which a portion of cells have a much higher level of expression of the antigen when compared to cells having a lower level of expression. Hence, the terms positive or negative are to be understood as being relative, i.e. positive cells have a much higher expression level as compared to cells being negative. Cells being negative in this sense may thus still have an expression level which may be detected. Expression on the surface of cells may be analysed using Fluorescence Activated Cell Sorting (FACS), and many specific antibodies are commercially available, e.g. such as for CD3, CD4, CD8, αβTCR, γδTCR and γ9δ2TCR, that are suitable for such FACS analysis, such as described in the examples and as available. γ9δ2T-cells can hence also be defined and selected as being positive for γ9δ2TCR in FACS. Antibodies suitable for FACS or similar separation techniques (such as e.g. antibodies conjugated to magnetic beads) are widely available. Conditions are selected, such as provided by the antibody manufacturer that allows the selection of negative and/or positive cells. Examples of antibodies that may be suitable for selection of γ9δ2-T cells, or engineered γ9δ2T cells such as available from BD Pharmingen (BD, 1 Becton Drive, Franklin Lakes, N.J. USA) are Vγ9-PE (clone B3, #555733), Vβ2-FITC (clone B6, #555738), γδTCRAPC (clone B1, #555718) or such as available from Beckman Coulter is pan-γδTCR-PE (clone IMMU510, # IM1418U) Similarly, suitable antibodies for αβ-T cell selection, such as anti-CD3 antibodies may be such as available from BD Pharmingen is CD3-FITC (#345763) or such as anti-αβTCR antibodies such as available from Beckman Coulter is pan-αβTCR-PE (#A39499) or pan-αβTCR-PC5 (#A39500).

Accordingly, in the method of the invention, first T-cells are provided. The T-cells may be primary cells, for example from a subject, such as described in the examples for a human subject. The T-cells may be αβ T-cells. The T-cells may also be cell lines, such as SupT-1, Jurkat, or Raji cells or any other widely available cell line. Any cell type, being a primary cell or any other cell line will suffice, as long as the cell population, or a substantial part thereof, expresses the T-cell receptor, i.e. such as being positive for the αβT-cell receptor in a FACS sorting or the like as described above, such a cell population may be contemplated. Also, any cell or cell population may be contemplated that, when provided with a γ9δ2TCR receptor according to the invention is capable of forming a functional TCR complex and exerting e.g. a functional cytoxic response and/or cytokine production. The cell that is provided may also be a progenitor cell, preferably a blood progenitor cell such as a thymocyte or a blood stem cell, which after it has been provided with the right stimuli can develop into T cells or engineered T cells. Hence it is understood that providing T cells and providing these with the γ9δ2TCR receptor according to the invention may also comprise providing progenitor cells, providing these with the γ9δ2TCR receptor and stimulating these progenitor cells such that these develop into engineered T-cells.

Also, a nucleic acid sequence is provided encoding a γ9-T-cell receptor chain wherein the γ9-CDR3 encoding region is randomly modified and a nucleic acid sequence encoding a δ2-T-cell receptor chain wherein the δ2-CDR3 encoding region is randomly modified. Preferably, the γ9-T-cell receptor chain and the δ2-T-cell receptor chain are of human origin. The human CDR3 regions of γ9 and δ2 are well defined. For example, the human CDR3 region of the γ9-TCR chain of amino acid sequence SEQ ID NO. 1 corresponds to amino acid residues 118-132, which corresponds to amino acid residues γ105-γ117 according to the International Immunogenetics Information System (IMGT). The human CDR3 region of the δ2 TCR chain of amino acid sequence SEQ ID NO. 2 corresponds to amino acid residues 112-127 which corresponds to amino acid residues δ105-δ117 according to the IMGT. According to the Internation Immunogenetics Information System (IMGT) (Lefranc MP. IMGT, the international ImMunoGeneTics database. Nucleic Acids Res. 2003; 31:307-310, which is incorporated herein by reference) the human CDR3 region may be delimited by, but does not include, the anchor positions C104 and F118, see also table 3, which are referred to for each chain as γC104 and γF118 and δC104 and δF118. The anchor positions γC104 corresponds to C117 in SEQ ID NO. 1 and γF118 corresponds to F133 in SEQ ID NO. 1. The anchor position δC104 corresponds to C111 of amino acid sequence SEQ ID NO. 2 and the anchor position δF118 corresponds to F128 of amino acid sequence SEQ ID NO. 2. The IMGT provides a common access to sequence, genome and structure for instance of T cell receptors of different species including human T cell receptors and allows the identification of a γ9T-cell receptor chain and a δ2T-cell receptor chain including the CDR3 regions, e.g. via the anchor positions.

According to the IMGT, the CDR3 is delimited by (but does not include) the anchor positions 2nd-CYS 104 and J-PHE or J-TRP 118. The JUNCTION includes 2nd-CYS 104 and J-PHE or J-TRP 118 and is therefore two amino acids longer than the CDR3. The CDR3 numbering goes from 105 to 117 and, if necessary, gaps or additional positions are added at the top of the loop. Note that, the J-PHE or J-TRP belongs to the characteristic J-REGION motif 'F/W-G-X-G' at positions 118-121, and that the CDR3 is delimited by the same anchor positions (2nd-CYS 104 and J-PHE or J-TRP 118), whatever the receptor type (IG or TR), the chain type (heavy or light for IG; alpha, beta, gamma or delta for TR) or the species. See also imgt.org/IMGTScientificChart/Numbering/IMGTIGVLsuperfamily.html for an explanation of the IMGT numbering. This IMGT numbering is also used in the examples.

Hence, by using the anchor positions, according to the IMGT standards, CDR3 regions can easily be identified. For example via entering an amino acid sequence (or nucleic acid sequence) using available online tools such as provided by IMGT (for example IMGT/V-QUEST) a γ9T-cell receptor chain sequence or a δ2T-cell receptor chain sequence can easily be identified as well as the exact CDR3 regions. Alternatively, γ9T-cell receptor chain sequences or δ2T-cell receptor chain sequences already publicly available can be found in the IMGT and hence, the CDR3 regions can be easily identified therefrom. Alternatively, using SEQ ID NO. 1 and SEQ ID No. 2 as a reference sequence and the anchor amino acid residue positions therein, the CDR3 regions of other γ9-T-cell and δ2-T-cell receptor chains are easily identified via an alignment, such as depicted for different CDR3 region in table 3. Hence, the skilled person can easily identify any CDR3 region from any γ9T-cell receptor chain sequence that corresponds with the CDR3 region from SEQ ID NO. 1, and also the skilled person can easily identify any CDR3 region from any δ2T-cell receptor chain sequence that corresponds with the CDR3 regions from SEQ ID NO. 2. Hence, the skilled person knows which amino acid sequence from any γ9-T-cell and/or δ2-T-cell receptor chains he needs to randomly modify.

Hence, modifying the δ2-CDR3 encoding region in a δ2-T-cell receptor chain nucleic acid sequence may comprise aligning the nucleic acid sequence of SEQ ID NO. 4 to the δ2-T-cell receptor chain nucleic acid sequence of interest, identifying the codons in the δ2-T-cell receptor chain nucleic acid sequence corresponding to the codons encoding the anchor positions in SEQ ID NO. 4, and randomly modifying the nucleic acid sequence in between the anchor positions codons identified in the δ2-T-cell receptor chain nucleic acid sequence of interest. Also, modifying the γ9-CDR3 encoding region in a γ9-T-cell receptor chain nucleic acid sequence may comprises aligning the nucleic acid sequence of SEQ ID NO. 4 to the γ9-T-cell receptor chain nucleic acid sequence of interest, identifying the codons in the γ9-T-cell receptor chain nucleic acid sequence corresponding to the codons encoding the anchor positions in SEQ ID NO. 3, and randomly modifying the nucleic acid sequence in between the anchor positions codons identified in the γ9-T-cell receptor chain nucleic acid sequence of interest. The random modification of the nucleic acid sequence of the CDR3 encoding regions is such that the amino acid sequence encoded by the nucleic acid sequence is modified, i.e. at least one amino acid residue is changed in another amino acid residue, or at least one amino acid residue is inserted or deleted.

The nucleic acid sequences encoding the γ9-T-cell receptor chain and the δ2-T-cell receptor chain may be introduced into T-cells to provide for an engineered T-cell with a γ9δ2T-cell receptor comprising the γ9-T-cell receptor chain and the δ2-T-cell receptor chain. By expressing the γ9-T-cell receptor chain and the δ2-T-cell receptor chain of which the CDR3 regions have been randomly modified, a specific γ9δ2-T-cell receptor is expressed in the cell. Optionally, the steps of providing a CDR3 randomly modified γ9-T-cell receptor chain and δ2-T-cell receptor chain and subsequent introduction into T-cells may be repeated. For example, each time this is done a different combination of randomly modified CD3 regions is used. It is also envisioned that the steps of repeating the steps, e.g. with different combinations of randomly modified CD3 regions, may be performed, at least in part, simultaneously. For example, a plurality of nucleic acid sequences encoding a γ9-T-cell receptor chain wherein the γ9-CDR3 encoding region is randomly modified and a nucleic acid sequence encoding a δ2-T-cell receptor chain wherein the δ2-CDR3 encoding region is randomly modified, may be provided, and this plurality of nucleic acid sequences may be introduced in T-cells thereby providing a plurality of engineered T-cells.

The anti-tumour response of the provided engineered T-cell expressing a γ9δ2T-cell receptor or an engineered γ9δ2T-cell receptor that mediate anti-tumour responses is identified. In case the steps of providing the nucleic acid sequences and introduction into the T-cells is performed in separate steps, the step of determining the anti-tumour responses and identifying the engineered γ9δ2T-cell receptor may be combined because it is known which nucleic acid sequences were introduced in each of the corresponding engineered γ9δ2T-cell. Determining the anti-tumour responses may hence be performed for each engineered γ9δ2T-cell separately. Alternatively, for example when engineered γ9δ2T-cells are combined, e.g. when repeating the steps such as described above is performed simultaneously, and a plurality of engineered T-cells is provided, the engineered T-cells may be separated and the anti-tumour response determined for each of the separated engineered T-cells. The engineered T-cells may be separated over different compartments and in each of the compartments the anti-tumour response may be determined. In such a scenario, the step of identifying the engineered T-cells that mediate anti-tumour responses may involve determining the sequence, e.g. via sequencing, of the nucleic acid sequence encoding each of the CDR3 regions of the γ9δ2TCR. Hence, optionally as a final step, identifying engineered T-cells that mediate anti-tumour responses involves determining the nucleic acid sequence encoding the γ9-T-cell receptor chain comprising the γ9-CDR3 encoding region and the nucleic acid sequence encoding the δ2-T-cell receptor chain comprising the δ2-CDR3 encoding region. It may also be envisioned to only determine the nucleic acid sequence of both of the γ9-CDR3 and the δ2-CDR3 encoding regions, i.e. it is not required to determine the complete nucleic acid sequences of the γ9-T-cell receptor chain and/or the δ2-T-cell receptor chain. As an alternative to determining the nucleic acid sequence, the amino acid sequences of the γ9-CDR3 and the δ2-CDR3 region may also be determined.

Preferably, the nucleic acid sequence encoding a γ9-T-cell receptor chain encodes an amino acid sequence having at least 60% sequence identity with the amino acid sequence of SEQ ID NO. 1, and wherein the nucleic acid sequence encoding a δ2-T-cell receptor chain encodes an amino acid sequence having at least 60% sequence identity with the amino acid sequence of SEQ ID NO. 2. The nucleic acid sequence encoding a γ9-T-cell receptor chain comprises preferably a nucleic acid sequence encoding an amino acid sequence having at least 70, 80, 90, 95 or 99% sequence identity with the amino acid sequence of SEQ ID NO. 1. The nucleic acid sequence encoding a δ2-T-cell receptor chain comprises preferably a nucleic acid sequence encoding an amino acid sequence having at least 70, 80, 90, 95 or 99% sequence identity with the amino acid sequence of SEQ ID NO. 2. The skilled person is capable of defining a γ9δ2-T-cell receptor with respect to function. Preferably, the percentage of sequence identity is calculated over the entire length of SEQ ID NO. 1 or SEQ ID NO. 2.

Random modification of the CDR3 regions of the γ9-CDR3 and δ2-CDR3 may comprise the arbitrary selection of amino acid residues. Such arbitrary selection may be done by generating random sequences in vitro, e.g. by random chemical synthesis, such as provided by Sloning Biotechnology using chemical synthesis (Sloning BioTechnology GmbH-A Division of MorphoSys, Zeppelinstrasse 4, 82178 Puchheim, Germany). Random modification of the CDR3 regions of the γ9-CDR3 and δ2-CDR3 may also comprise the arbitrary selection from sequences found in natural CDR3 regions. Such natural CDR3 amino acid sequences are generated randomly, i.e. arbitrarily selected, by nature.

With regard to the random modification, the randomly modified γ9-CDR3 encoding region may preferably be modified at the amino acid sequence corresponding to amino acid residues 118-132 of SEQ ID NO 1. With regard to the random modification, the randomly modified γ9-CDR3 encoding region may preferably be modified at the amino acid sequence corresponding to amino acid residues 122-124 of SEQ ID NO 1. As said, a γ9-CDR3 encoding region is easily identified, e.g. via alignment and/or from information as provided by IMGT, and hence the amino acid residues from a γ9-CDR3 encoding region corresponding to the amino acid residues 118-132 of SEQ ID NO. 1 as well. Optionally, amino acid residues C117 and F133 of SEQ ID NO. 1 may further be used for identifying the corresponding amino acid residues. In an alignment, such as depicted in table 3, the amino acid residues of a γ9-CDR3 encoding region corresponding to amino acid residues 118-132 of amino acid sequence SEQ ID NO. 1 can easily be identified, and thus amino acid residues corresponding to amino acid residues 122-124 of SEQ ID NO 1 as well. Hence, a corresponding sequence may be easily identified via aligning the amino acid sequence of interest to the reference amino acid sequence (SEQ ID NO. 1), and identifying the anchor amino acid residues C117 and F133, so that the CDR3 region is identified. Next, the CDR3 regions are aligned and the amino acid residues of the amino acid sequence that correspond to 118-132 of SEQ ID NO. 1 is identified. With regard to the random modification, the randomly modified δ2-CDR3 encoding region may be modified at the amino acid sequence corresponding to amino acid residues 115-122 of SEQ ID NO. 2. With regard to the random modification, the randomly modified δ2-CDR3 encoding region may be modified at the amino acid sequence corresponding to amino acid residues 112-127 of SEQ ID NO. 2. A δ2-CDR3 encoding region may be easily identified, e.g. via alignment and/or from information as provided by IMGT, and hence the amino acid residues from a δ2-CDR3 encoding region corresponding to the amino acid residues 112-127 of SEQ ID NO. 2 as well. Optionally, amino acid residues C111 and F128 of SEQ ID NO. 2 may further be used for identifying the corresponding amino acid residues. In an alignment, such as depicted in table 3, the amino acid residues of a δ2CDR3 encoding region corresponding to amino acid residues 112-127 of amino acid sequence SEQ ID NO. 2 can easily be identified. Hence, a corresponding sequence may be easily identified via aligning the amino acid sequence of interest to the reference amino acid sequence (SEQ ID NO. 2), and identifying the anchor amino acid residues C111 and F128, such that the CDR3 region is identified. Next, the CDR3 regions are aligned and the amino acid residues of the amino acid sequence that correspond to 112-127 of SEQ ID NO. 2 can bes identified, and thus the amino acid sequence that correspond to amino acid residues 115-122 as well.

In one embodiment, randomly modifying the amino acid sequence corresponding to amino acid residues 115-122 of SEQ ID NO. 2 comprises a modification in length.

In one embodiment, randomly modifying the amino acid sequence corresponding to amino acid residues 112-127 of SEQ ID NO. 2 comprises a modification in length.

In one embodiment, randomly modifying the amino acid sequence comprises introducing amino acid substitutions, deletions, and/or insertions.

With regard to the random modification, this may include any modification such as amino acid substitution, deletion and/or insertion. Hence, the random modification may include a modification in sequence and/or length. The CDR3 regions may thus vary in length ranging from 1, 2, 3, 4, 5, 6, 7, 8, 9, 10, 11, 12, 13, 14, 15, 16, 17, 18, 19, 20, 21 or 22 amino acid residues. Preferably, the δ2-CDR3 encoding region may vary in length ranging from 5-7 amino acids between positions δL109 and δT113 according to the IGMT annotation. Hence, preferably the δ2-CDR3 encoding region corresponding to amino acid sequence 112-127 of SEQ ID NO. 2 is randomly modified between L116 and T123 of SEQ ID NO. 2 such that it contains 5-7 amino acids in this region. Hence, the entire δ2-CDR3 encoding region preferably varies in length ranging from 15-17 amino acid residues. Amino acid substitution may include any substitution such as conserved substitutions wherein one amino acid from a group is changed for another amino acid residue of the group, e.g. one aliphatic amino acid residue is exchange for another aliphatic amino acid residue, or a non-conserved substitution wherein one amino acid from a group is changed for another amino acid residue of a different group, e.g. one aliphatic amino acid residue is exchange for an basic amino acid residue.

With regard to providing a nucleic acid, it is understood that the nucleic acid is provided such that when it is introduced in a cell that it can be expressed such that the amino acid sequence it encodes is expressed on the surface of the cell. Preferably this is done by integrating the nucleic acid or nucleic acids into the genome of the cell. Preferably, the nucleic acid sequence encoding a γ9-T-cell receptor chain is provided in a genetic construct and the nucleic acid sequence encoding a δ2-T-cell receptor chain is provided in a genetic construct. The genetic constructs may be provided on separate vectors. The genetic constructs may also be provided on a single vector. The nucleic acid sequence encoding a γ9-T-cell receptor chain and the nucleic acid sequence encoding a δ2-T-cell receptor chain may also be provided in a single genetic construct. For example, a single genetic construct may express a single mRNA comprising an Internal Ribosomal Entry Site, such as described in the example, such that each receptor chain may be transcribed from the same mRNA.

The genetic construct and/or vectors may also comprise selectable markers. A selectable marker may be defined as any nucleic acid sequence and/or amino acid sequence that allows cells that are provided therewith to be selected. For example, selectable markers may be neomycine or puromycin resistance genes such as described in the examples. Selection of cells to which the genetic construct and/or vector has been transferred may than be performed by incubating in the presence of neomycine or puromycin. Other selectable markers may be for example any one of green, red and yellow fluorescent proteins. Selecting may than be performed by using FACS. It is not required to have a selectable marker, as the cell when expressing the γ9δ2T-cell receptor may be selected based on that expression on itself, e.g. via selection with an antibody directed thereto such as described above. It may be provided that the host cell does not express a substantial amount of the γ9δ2T-cell receptor to allow selection of engineered γ9δ2T-cells, i.e. expression of the endogenous γ9δ2-T-cell receptor must be much lower as compared with the engineered γ9δ2-T-cell receptor.

Preferably, the nucleic acid sequence encoding a γ9-T-cell receptor chain is provided in a retroviral vector and the nucleic acid sequence encoding a δ2-T-cell receptor chain is provided in a retroviral vector and the steps of introducing the nucleic acid sequences into the T-cells comprises retroviral vector transduction of the T-cells. The transduction may be performed simultaneously or in subsequent steps.

Alternatively, the nucleic acid sequence encoding a γ9-T-cell receptor chain and the nucleic acid sequence encoding a δ2-T-cell receptor chain are provided in a single retroviral vector, and the steps of introducing the nucleic acid sequences into the T-cells comprises retroviral vector transduction of the T-cells. Retroviral vectors, such as described in the examples, are highly efficient for transferring the nucleic acid sequences to the T-cells such that engineered T-cells can be provided. Many retroviral and lentiviral vectors are known or such as described in the examples. Retroviral vectors have an RNA genome which, when entered in a cell, is reverse transcribed into DNA that is subsequently integrated into the host genome. Integration is advantageous as it allows to proliferation of transduced cells while maintaining the viral vector genome comprising the genetic construct.

In one embodiment, the step of determining the anti-tumour reactivity comprises contacting the cells with tumour cells. Tumour cells may be any kind of tumour cells. For example, primary tumour cells from a patient. The tumour cells may be tumour cells from cell lines, such as the cell lines listed in the examples named Daudi, RPMI8226/S, OPM2, LME1, K562, Saos2, MZ1851RC, SCC9, Fadu, MDA-MB231, MCF7, BT549, SW480, which are well known in the art. Tumour cell lines may easily be obtained from the American Type Culture Collection (ATCC, Manassas, Va.) and the like. The step of determining anti-tumour activity may include any assay in which an anti-tumour effect may be determined, such as having an effect on tumour cell division rate, i.e. the speed with which the tumour cells divide, cell death, binding to the tumour cells etc.

Determining the anti-tumour responses includes contacting the engineered T-cell with a tumour cell and measuring its ability to lyse the tumour cell and/or induce IFN-γ production. The ability to lyse the tumour cells include providing a fixed amount of tumour cells with which the engineered γ9δ2 T-cell, i.e. an engineered T-cell expressing a γ9δ2TCR, is contacted and after an incubation period the number of viable tumour cells is counted. When the number of viable cells counted is compared to a control not contacted with the engineered γ9δ2 T-cell, and the number is lower, such an engineered γ9δ2 T-cell can be regarded to have an anti-tumour response. In addition to counting the viable cells, one may also perform a $^{51}$Chromium-release assay similarly to what is described in the examples. The amount of $^{51}$Chromium release being a measure of the number of cells that have been lysed.

Similarly, IFN-γ production may also be determined, e.g. via antibody staining, ELISA and/or quantitative PCR for the expressed mRNA. Assays for determining IFN-γ are commercially widely available, such as described in the example. Engineered γ9δ2 T-cells are contacted with the tumour cells. The contacting may be in the presence of a phosphoantigen, such as pamidronate. Hence, when the amount of IFN-γ produced is higher as compared to when cells are not contacted with the engineered γ9δ2 T-cell, such an engineered γ9δ2 T-cell may be regarded as having an anti-tumour response. In addition to comparing with a control, i.e. to cells not contacted with the engineered γ9δ2 T-cell, one may also compare with a reference value. In any case, any assay in which an effect on tumour cells may be determined involving contacting the γ9δ2 T-cell with the tumour cell may be contemplated. As long as an anti-tumour effect, such as induction of cell death, cell viability, binding to the tumour cell, and/or IFN-γ production may be determined.

Furthermore, with regard to the methods described above, the T cells may be expanded before or after the transfer of the nucleic acids encoding the engineered γ9δ2 T-cell receptor, i.e. with the randomly modified CDR3 regions. Preferably, the expansion is after the transfer such that relatively little nucleic acids need to be transferred. This expansion of the T cells may be performed by stimulation with α-CD3/CD28 Dynabeads in the presence of IL-2. A rapid expansion protocol such as described in the examples may also be used. The expanded cells comprising the engineered γ9δ2 T-cell receptor, which may be selected e.g. via a selectable marker such as described above, may be further selected for the presence of the CD4 antigen and the CD8 antigen, e.g. using the MACS separating system as described in the examples. The engineered T-cells may be subsequently further expanded using the REP protocol as described by Riddel and Greenberg, 1990 J Immunol Methods. 128(2):189-201, which is incorporated herein by reference, or using similar further expansion methods thereto. Briefly, the expansion method involves using antibodies directed against T cell activation molecules, such as TCR, CD3 and CD28 and/or feeder cells and/or stimulating cytokines.

In another embodiment, a γ9δ2T-cell receptor, or a fragment thereof, is provided comprising a γ9-T-cell receptor chain comprising a γ9-CDR3 region, wherein the amino acid sequence of the γ9-CDR3 region corresponding to amino acid residues 122-124 of SEQ ID NO. 1 is modified and a δ2-T-cell receptor chain comprising a δ2-CDR3 region wherein the amino acid sequence of the δ2-CDR3 region corresponding to amino acid residues 115-122 of SEQ ID NO. 2 is modified, wherein the combinations of the amino acid modifications within the γ9δ2T-cell receptor, or a fragment thereof, are as listed in Table 1. The substitutions may comprise the combinations such as listed in table 1. The amino acid sequences of the respective γ9-CDR3 and δ2-CDR3 regions are substituted with amino acid sequences selected from the group consisting of combinations of amino acid sequences AQQ (γ9) and ALKRTD (δ2); AQQ (γ9) and LLGY(δ2); IQ (γ9) and ALKRTD (δ2); and; IQ (γ9) and TLGMGGEY(δ2). These γ9δ2T-cell receptors, or fragments thereof, comprising these particular combinations of CDR3 regions, were identified using the methods according to the invention such as described above and as described in the examples.

Combinations of amino acid sequences of γ9-CDR3 and δ2-CDR3 regions that may be preferably combined are listed below in table 1 as they show an anti-tumour effect. Table 1. Combinations of amino acid sequences of γ9-CDR3 and δ2-CDR3 regions. The region corresponding to amino acid residues of the γ9-CDR3 region corresponding to number 122-124 of SEQ ID NO. 1 which has been substituted, i.e. has been modified, is listed, and the region corresponding to amino acid residues of the δ2-CDR3 region corresponding to amino acid residues 115-122 of SEQ ID NO. 2 which has been substituted is listed as well. The different combinations of γ9-CDR3 and δ2-CDR3 are numbered from 1-4. For example, number 2 corresponds to a γ9δ2TCR with a γ9-T-cell receptor chain wherein the γ9-CDR3 region corresponding to number 122-124 of SEQ ID NO. 1 has been substituted with AQQ and a δ2T-cell receptor chain wherein the δ2-CDR3 region corresponding to amino acid residues 115-122 of SEQ ID NO. 2 has been substituted with ALKRTD.

TABLE 1

Combinations of modified amino acid sequences of γ9-CDR3 and δ2-CDR3 regions, wherein the listed amino acid sequences substitute γ9-CDR3 amino acid residues corresponding with 122-124 of SEQ ID NO. 1 and substitute δ2-CDR3 amino acid residues corresponding with 115-122 of SEQ ID NO. 2.

| Nr. | combination | γ9-CDR3 | δ2-CDR3 |
|---|---|---|---|
| 1 | γ9-cl5/δ2-cl5 | IQ (SEQ ID NO. 20) | ALKRTD (SEQ ID NO. 15) |
| 2 | γ9-G115/δ2-cl5 | AQQ (SEQ ID NO. 21) | ALKRTD (SEQ ID NO. 15) |
| 3 | γ9-cl5/δ2-G115 | IQ (SEQ ID NO. 20) | TLGMGGEY (SEQ ID NO. 19) |
| 4 | γ9-G115/δ2-cl3 | AQQ (SEQ ID NO. 21) | LLGY (SEQ ID NO. 22) |

In another embodiment, a γ9δ2T-cell receptor, or a fragment thereof, is provided comprising a γ9-T-cell receptor chain comprising a γ9-CDR3 region, wherein the amino acid sequence of the γ9-CDR3 region corresponding to amino acid residues 118-132 of SEQ ID NO. 1 is modified and a δ2-T-cell receptor chain comprising a δ2-CDR3 region wherein the amino acid sequence of the δ2-CDR3 region corresponding to amino acid residues 112-127 of SEQ ID NO. 2 is modified, wherein the combinations of the amino acid modifications within the γ9δ2T-cell receptor, or a fragment thereof, are as listed in Table 2. The substitutions may comprise the combinations such as listed in table 2. The amino acid sequences of the respective γ9-CDR3 and δ2-CDR3 regions are substituted with amino acid sequences selected from the group consisting of combinations of amino acid sequences ALWEIQELGKKIKV (γ9) and ACDALKRTDTDKLI (δ2); ALWEAQQELGKKIKV (γ9) and ACDALKRTDTDKLI (δ2); ALWEIQELGKKIKV (γ9) and ACDTLGMGGEYTDKLI (δ2); ALWEAQQELGKKIKV (γ9) and ACDLLGYTDKLI (δ2). These γ9δ2T-cell receptors, or fragments thereof, comprising these particular combinations of CDR3 regions, were identified using the methods according to the invention such as described above and as described in the examples.

Combinations of amino acid sequences of γ9-CDR3 and δ2-CDR3 regions that may be preferably combined are listed below in table 2 as they show a strong anti-tumour effect. Table 2. Combinations of amino acid sequences of γ9-CDR3 and δ2-CDR3 regions. The region corresponding to amino acid residues of the γ9-CDR3 region corresponding to number 118-132 of SEQ ID NO. 1 which has been substituted, i.e. has been modified, is listed, and the region corresponding to amino acid residues of the δ2-CDR3 region corresponding to amino acid residues 112-127 of SEQ ID NO. 2 which has been substituted, i.e. is modified, is listed as well. The different combinations of γ9-CDR3 and δ2-CDR3 are numbered from 1-4 in table 2. For example, number 2 corresponds to a γ9δ2TCR with a γ9-T-cell receptor chain wherein the γ9-CDR3 region corresponding to number 118-132 of SEQ ID NO. 1 has been modified to (substituted with) ALWEAQQELGKKIKV and a δ2T-cell receptor chain wherein the δ2-CDR3 region corresponding to amino acid residues 112-127 of SEQ ID NO. 2 has been modified to (substituted with) ACDALKRTDTDKLI.

TABLE 2

Combinations of complete modified amino acid sequences of γ9-CDR3 and δ2-CDR3 regions

| Nr. | combination | γ9-CDR3 | δ2-CDR3 |
|---|---|---|---|
| 1 | γ9-c15/<br>δ2-c15 | ALWEIQELGKKIKV<br>(SEQ. ID NO. 16) | ACDALKRTDTDKLI<br>(SEQ. ID NO. 17) |
| 2 | γ9-G115/<br>δ2-c15 | ALWEAQQELGKKIKV<br>(SEQ. ID NO. 3) | ACDALKRTDTDKLI<br>(SEQ. ID NO. 17) |
| 3 | γ9-c15/<br>δ2-G115 | ALWEIQELGKKIKV<br>(SEQ. ID NO. 16) | ACDTLGMGGEYTDKLI<br>(SEQ. ID NO. 4) |
| 4 | γ9-G115/<br>δ2-c13 | ALWEAQQELGKKIKV<br>(SEQ. ID NO. 3) | ACDLLGYTDKLI<br>(SEQ. ID NO. 18) |

In one embodiment, the γ9δ2T-cell receptor, or a fragment thereof, comprises a γ9-T-cell receptor chain comprising a γ9-CDR3 region, wherein the amino acid sequence of the γ9-CDR3 region corresponding to amino acid residues 122-124 of the amino acid sequence of SEQ ID NO. 1 is AQQ, and a δ2-T-cell receptor chain comprising a δ2-CDR3 region wherein the amino acid sequence of the δ2-CDR3 region corresponding to amino acid residues 115-122 of the amino acid sequence of SEQ ID NO. 2 is ALKRTD. In a further embodiment, the γ9δ2T-cell receptor, or a fragment thereof, comprises a γ9-T-cell receptor chain comprising a γ9-CDR3 region, wherein the amino acid sequence of the γ9-CDR3 region corresponding to amino acid residues 118-132 of the amino acid sequence of SEQ ID NO. 1 is ALWEAQQEL-GKKIKV, and a δ2-T-cell receptor chain comprising a δ2-CDR3 region wherein the amino acid sequence of the δ2-CDR3 region corresponding to amino acid residues 112-128 of the amino acid sequence of SEQ ID NO. 2 is ACDALKRTDTDKLI. This particular combination of CDR3 regions in the γ9δ2T-cell receptor, or fragment thereof has shown a particular high anti-tumour activity and may hence be preferred.

In one embodiment, the γ9δ2T-cell receptor or fragment thereof according to invention, wherein the amino acid sequence of the γ9-CDR3 region corresponding to amino acid residues 118-121 of the amino acid sequence of SEQ ID NO. 1 is ALWE, and wherein the amino acid sequence of the γ9-CDR3 region corresponding to amino acid residues 125-132 of the amino acid sequence of SEQ ID NO. 1 is ELGKKIKV, and wherein the amino acid sequence of the δ2-CDR3 region corresponding to amino acid residues 112-114 of the amino acid sequence of SEQ ID NO. 2. is ACD, and wherein the amino acid sequence of the δ2-CDR3 region corresponding to amino acid residues 123-127 of the amino acid sequence of SEQ ID NO. 2 is TDKLI. It is understood that these amino acid sequences correspond to the sequences which are flanking the amino acid sequences that are to be substituted with the amino acid sequences as listed above.

In a further embodiment, a γ9δ2T-cell receptor, or fragment thereof, is provided, wherein the γ9-T-cell receptor chain comprises an amino acid sequence having at least 60%, 70%, 80%, 90%, 95%, 99%, or 100% sequence identity with the amino acid sequence of SEQ ID NO. 1, and/or wherein the δ2-T-cell receptor chain comprises an amino acid sequence having at least 60%, 70%, 80%, 90%, 95%, 99%, or 100% sequence identity with the amino acid sequence of SEQ ID NO. 2. It is understood that the amino acid sequence of the γ9-CDR3 region corresponding to amino acid residues number 122-124 of SEQ ID NO. 1, and the amino acid sequence of the δ2-CDR3 region corresponding to amino acid residues 115-122 of SEQ ID NO. 2, are in this embodiment substituted in accordance with Table 1.

In one embodiment, a γ9δ2T-cell receptor, or fragment thereof is provided, wherein the γ9-T-cell receptor chain comprises an amino acid sequence comprising amino acid residues 1-121 and 125-315 of the amino acid sequence of SEQ ID NO. 1 and wherein the modified amino acid residues 122-124 are as defined Table 1, and wherein the δ2-T-cell receptor chain comprises an amino acid sequence comprising amino acid residues 1-114 and 123-292 of the amino acid sequence of SEQ ID NO. 2 and wherein the modified amino acid residues 115-122 are as defined in Table 1. It is understood that the amino acid sequence of the γ9-CDR3 region corresponding to amino acid residues number 122-124 of SEQ ID NO. 1, and the amino acid sequence of the δ2-CDR3 region corresponding to amino acid residues 115-122 of SEQ ID NO. 2, are in this embodiment substituted in accordance with Table 1.

It is understood that the amino acid sequences SEQ ID NO. 1 and SEQ ID NO. 2 each comprise a leader sequence. The leader sequence of amino acid sequence SEQ ID NO. 1 is from amino acid Nr. 1-20 of SEQ ID NO. 1. The leader sequence of amino acid sequence SEQ ID NO. 2 is from amino acid Nr. 1-19 of SEQ ID NO. 2. The leader sequence may directs the amino acid chain to the surface of the cell. The leader sequence can be cleaved from the nascent amino acid chain and is not present in the final protein. Hence, in one embodiment, a γ9δ2T-cell receptor, or fragment thereof is provided, wherein the γ9-T-cell receptor chain comprises an amino acid sequence comprising amino acid residues 21-121 and 125-315 of the amino acid sequence of SEQ ID NO. 1 and wherein the modified amino acid residues 122-124 are as defined in Table 1, and wherein the δ2-T-cell receptor chain comprises an amino acid sequence comprising amino acid residues 20-114 and 123-292 of the amino acid sequence of SEQ ID NO. 2 and wherein the modified amino acid residues 115-122 are as defined in Table 1. It is understood that the amino acid sequence of the γ9-CDR3 region corresponding to amino acid residues number 122-124 of SEQ ID NO. 1, and the amino acid sequence of the δ2-CDR3 region corresponding to amino acid residues 115-122 of SEQ ID NO. 2, are in this embodiment substituted in accordance with Table 1. It is also understood that it may be optional to use alternative leader sequences, and it is also understood that this leader sequences from SEQ ID NO. 1 and SEQ ID NO. 2 may be disregarded, e.g. when comparing sequences and/determining corresponding sequences and/or alignment and/or determining percentages of identity.

In another embodiment, a conjugate is provided comprising a soluble fragment of the γ9δ2T-cell receptor according to any one of the γ9δ2T-cell receptors as described above. The extracellular domain of the γ9δ2-T-cell receptor comprises the amino acid sequence of the γ9-T-cell receptor chain corresponding to amino acid residues 21-263 of the amino acid sequence of SEQ ID NO. 1 and the amino acid sequence of the δ2-T-cell receptor chain corresponding to amino acid residues 20-249 of the amino acid sequence of SEQ ID NO. 2. The conjugate may be linked to an agent. Preferably, the agent is selected from the group consisting of a diagnostic agent, a therapeutic agent, an anti-cancer agent, a chemical, a nanoparticle, a chemotherapeutic agent or a fluorochrome. Such conjugates that may be linked to substrates (e.g. chemicals, nanoparticles) may be used e.g. to deliver chemotherapy to a target of interest. In addition, in diagnostics expression of defined ligands may be tested by taking advantage of the soluble TCRs linked to fluorochromes which are then used as staining tool or for the biochemical isolation of the ligand.

Furthermore, in this embodiment, the invention provides for isolated nucleic acid sequences encoding the δ2-T-cell receptor chain, or fragment thereof, according to the invention, wherein the δ2-CDR3 region corresponding to amino acid residues 115-122 of the amino acid sequence SEQ ID NO. 2 is substituted with amino acid residues ALKRTD or LLGY. Hence, the δ2-CDR3 region corresponding to amino acid residues 112-127 of the amino acid sequence SEQ ID NO. 2 is substituted between D114 and T123 of SEQ ID NO. 2 with amino acid residues ALKRTD or LLGY. The invention further provides for an isolated nucleic acid sequence encoding the γ9-T-cell receptor chain, or fragment thereof, according to the invention, wherein the amino acid sequence of the γ9-CDR3 region corresponding to amino acid residues 122-124 of the amino acid sequence SEQ ID NO. 1 is substituted with amino acid residues IQ. Hence, the γ9-CDR3 region corresponding to amino acid residues 118-132 of the amino acid sequence SEQ ID NO. 1 is substituted between E121 and E 125 of SEQ ID NO 1 with amino acid residues IQ.

Also are provide genetic constructs comprising the isolated nucleic acid sequences according to the invention, and retroviral vectors comprising the genetic construct.

For example, isolated nucleic acid sequences are listed as SEQ ID NO. 3 and SEQ ID NO. 4 and correspond respectively to open reading frames of the γ9-T-cell receptor chain (encoding corresponding amino acid sequence SEQ ID NO. 1) and the δ2-T-cell receptor chain (encoding corresponding amino acid sequence SEQ ID NO. 2) of the G115wt clone, such as described in the examples. These isolated nucleic acid sequences, when being part of an expression cassette may be interspersed by for example intronic encoding sequences, and have 5' and 3' non-coding regions. When such sequences are expressed, the corresponding γ9-T-cell receptor chain and the δ2-T-cell receptor chain amino acid sequences are made in the cell. Hence, the nucleic acid sequence of SEQ ID NO. 3 encodes the amino acid sequence of SEQ ID NO. 1. The nucleic acid sequence of SEQ ID NO. 4 encodes the amino acid sequence of SEQ ID NO. 2. The amino acid sequences of SEQ ID NO. 1 and SEQ ID NO. 2 as they are formed in the cell each comprise a leader sequence. The leader sequence of amino acid sequence SEQ ID NO. 1 is from amino acid Nr. 1-20 of SEQ ID NO. 1. The leader sequence of amino acid sequence SEQ ID NO. 2 is from amino acid Nr. 1-19 of SEQ ID NO. 2. The leader sequence may directs the amino acid chain to the surface of the cell. The leader sequence can be cleaved from the nascent amino acid chain and is not present in the finished protein. The constant domain of an engineered γ9δ2T-cell receptor may have short connecting sequences in which cysteine residues form a disulfide bond, forming a link between the γ9-TCR chain and the δ2-TCR chain. For example, C263 of amino acid sequence SEQ ID NO. 1 and C249 of amino acid sequence SEQ ID NO. 2, corresponding to the γ9-TCR chain and the δ2-TCR chain of G115wt may form a disulphide bond. A disulfide bond is a covalent bond formed by the coupling of two thiol groups of the cysteins.

In another embodiment, a nucleic acid sequence encoding the γ9δ2T-cell receptor, or fragment thereof, according to the invention is provided, as well as a nucleic acid sequence comprising genetic constructs or a genetic construct encoding the γ9δ2T-cell receptor according to the invention. It is understood that in this embodiment the nucleic acid sequences encoding the γ9δ2T-cell receptor are to be comprised in single nucleic acid sequence. Preferably, the nucleic acid sequence comprising the genetic construct or genetic constructs is comprised in a retroviral vector.

In one embodiment, a cell is provided expressing the soluble fragment of the γ9δ2T-cell receptor according to the invention.

In one embodiment, a T cell is provided comprising the γ9δ2T-cell receptor according the invention, i.e. corresponding to the specific γ9δ2T-cell receptors of which the CDR3 regions are substituted with the specific amino acid sequences such as listed and indicated above. In a further embodiment, the T cell comprises the isolated nucleic acid sequences as listed above, the genetic construct or genetic constructs according as listed above or the retroviral vector or retroviral vectors as listed above.

Furthermore, the γ9δ2T-cell receptor, or fragment thereof, according to the invention as described above, or a conjugate, an isolated nucleic acid sequence, or a genetic construct, or a retroviral vector, or a T cell, as listed above, is for use as a medicament. Preferably, the γ9δ2T-cell receptor, or fragment thereof, according to the invention as described above, or a conjugate, an isolated nucleic acid sequence, or a genetic construct, or a retroviral vector, or a T cell, as listed above, is for use as a medicament in the treatment of cancer.

It is understood that the specific γ9δ2T-cell receptors, or fragments thereof, according the invention, i.e. corresponding to the specific γ9δ2T-cell receptors of which the CDR3 regions are substituted with the specific amino acid sequences such as listed and indicated above, are in particular useful in medical treatments and/or in diagnostics. For example, immune cells may be redirected against cancer cells by e.g. ex vivo transfer of one of the specific γ9δ2T-cell receptors as listed into αβT-cells of a patient followed by expansion and adoptive transfer of these engineered T-cells back into the patient. Hence, immune cells may be redirected against cancer cells. This may also be done in in combination with any other receptors (e.g. NKG2D) in immune-cells in order to increase anti-cancer reactivity.

EXAMPLES

Materials and Methods

Cells and Cell Lines

PBMCs were isolated from buffy coats obtained from Sanquin Blood Bank (Amsterdam, The Netherlands). Primary AML blasts were received after obtaining informed consent from the LML biobank UMC Utrecht and a kind gift from Matthias Theobald (Mainz, Germany) and were collected according to GCP and Helsinki regulations. Cell lines are described in supplementary Material and Methods.

TCR Mutagenesis, Cloning and Sequencing

γ9δ2TCR modifications are based on codon-optimized genes of γ9- or δ2-TCR chain G115 flanked by NcoI and BamHI restriction sites (synthesized by GeneArt, Regensburg, Germany). To generate alanine-mutations, site-directed mutagenesis was performed by overlap extension PCR 21 or whole plasmid mutagenesis 22; 23, using a proofreading polymerase (Phusion, Bioke). Mutated NcoI-BamHI digested γ9- or δ2-TCR chains were ligated into the retroviral vector pBullet and sequenced by BaseClear (Leiden, The Netherlands).

Flow Cytometry

γ9δ2TCR expression was analyzed by flow cytometry using a Vδ2-FITC (clone B6, BD) or a pan-γδTCR-PE antibody (clone IMMU510, Beckman Coulter). Fold change was calculated based on MFI values of γ9-G115wt/δ2-G115wt transduced T-cells set to 1 and mock transduced T-cells to 0.

Functional T-Cell Assays

51Chromium-release assay for cell-mediated cytotoxicity was previously described. Target cells were labeled overnight with 100 μCu 51Cr (150 μCu for primary cells) and incubated for 5 h with transduced T-cells in five effector-to-target ratios (E:T) between 30:1 and 0.3:1. Fold change was calculated when compared to reactivity of engineered T-cells expressing unmutated γ9δ2TCR. IFN-γ ELISpot was performed using anti-huIFN-ymAb1-D1K (I) and mAb7-B6-1 (II) (Mabtech-Hamburg, Germany) following the manufacturer's recommended procedure. Target and effector cells (E:T 3:1) were incubated for 24 h in the presence of pamidronate (Calbiochem, Germany) where indicated. IFNγ ELISA was performed using ELISA-ready-go! Kit (eBioscience) following manufacturer's instructions. Effector and target cells (E:T 1:1) were incubated for 24 h in the presence of pamidronate as indicated. Where specified, fold change was calculated when compared to reactivity of engineered T-cells expressing unmutated γ9δ2TCR.

Retroviral Transduction of T-Cells

γ9δ2TCRs were transduced into αβT-cells as previously described (Marcu-Malina et al., 2011). In brief, packaging cells (phoenix-ampho) were transfected with gag-pol (pHIT60), env (pCOLT-GALV) (Stanislawski et al., 2001) and two retroviral constructs (pBullet) containing either γ9-chain-IRES-neomycine or δ2-chain-IRES-puromycine, using Fugene6 reagent (Takara, Gennevilliers, France). Human PBMC activated with αCD3 (30 ng/ml) (Orthoclone OKT3, Janssen-Cilag, Tilburg, The Netherlands) and IL2 (50 IU/ml) (Proleukin, Novartis, Arnhem, The Netherlands) were twice transduced with viral supernatant within 48 hours in the presence of 50 IU/ml IL-2 and 4 μg/ml polybrene (Sigma-Aldrich, Zwijndrecht, The Netherlands). Transduced T-cells were expanded by stimulation with αCD3/CD28 Dynabeads ($0.5 \times 10^6$ beads/$10^6$ cells) (Invitrogen) and IL-2 (50 IU/ml) and selected with 800 μg/ml geneticin (Gibco, Karlsruhe, Germany) and 5 μg/ml puromycin (Sigma-Aldrich, Zwijndrecht, The Netherlands) for one week. Where indicated polyclonal CD4+ and CD8+TCR transduced T-cells with were sorted based on CD4 or CD8 expression using CD4 and CD8 MACS separating system (Miltenyi Biotech, Bergish Gladbach, Germany). Following selection TCR-transduced T-cells were expanded in vitro based on a previously described REP protocol (Riddell and Greenberg, 1990).

Functional T-Cell Assays $^{51}$Chromium-release assay for cell-mediated cytotoxicity was previously described (Kuball et al., 2004). Target cells were labelled overnight with 100 μCu $^{51}$Cr (150 μCu for primary cells) and subsequently incubated with transduced T-cells in five effector to target ratios (E:T) between 30:1 and 0.3:1. After 4-6 h $^{51}$Cr-release was measured in the supernatant. Fold change was calculated based on $^{51}$Cr-release of γ9-G115wt/δ9-G115wt transduced T-cells normalized to 1; for side by side experiments based on γ9-3 wt/δ9-3 wt, γ9-5 wt/δ9-5 wt or γ9-G115wt/δ9-G115wt normalized to 1.

IFNγ ELISpot was performed using anti-hu IFN-γ mAb1-D1K (I) and mAb7-B6-1 (II) from Mabtech (Hamburg, Germany) following manufactures' recommended procedure (Besold et al., 2007). In all assays target and effector cells (E:T 3:1) were incubated for 24 h in the presence of pamidronate (Calbiochem, Germany) where indicated.

IFN-γELISA was performed using ELISA-ready-go! Kit (eBioscienc) following manufacturers' instructions. Effector and target cells (E:T 1:1) were incubated for 24 h in the presence of pamidronate as indicated. Where specified, fold change was calculated based on IFN-γ secretion γ9-G115wt/δ9-G115wt transduced T-cells normalized to 1; for the side by side experiments based on γ9-3 wt/δ9-3 wt, γ9-5 wt/δ9-5 wt or γ9-G115wt/δ9-G115wt normalized to 1.

Animal Models

To induce tumour xenografts, sublethal total body irradiated (2Gy), 11-17 weeks old RAG-2-/-/γc-/---BALB/C mice were injected i.v. with $0.5 \times 10^6$ Daudi-Luc cells (a kind gift from Genmab Utrecht, The Netherlands) or $5 \times 10^6$ RPMI8226/S-Luc cells (Anton Martens, Utrecht, The Netherlands) together with $10^7$ γ9δ2TCR+□ transduced T-cells. The RAG-2$^{-/-}$/γc$^{-/-}$-BALB/C mice were originally obtained from AMCAS b.v. (Amsterdam, the Netherlands). Mice were bred and housed in the specific pathogen-free (SPF) breeding unit of the Central Animal Facility of the University of Utrecht. All animal experiments were conducted according to Institutional Guidelines after acquiring permission from the local Ethical Committee for Animal Experimentation, and in accordance with current Dutch laws on Animal Experimentation. All mice developed tumours, mainly growing in the bone marrow visualized in vivo once a week by Biospace bioluminescent imaging. Mice were anesthetized by isoflurane inhalation before they received an intraperitoneal injection of 100 μl of 25 mg/ml Beetle Luciferin (Promega, USA). Bioluminescence images were acquired using a third generation cooled GaAs intensified charge-coupled device camera, controlled by the Photo Vision software and analyzed with M$^3$Vision software (all from Photon Imager;

Biospace Laboratory). Mice received $0.6 \times 10^6$ IU of IL2 (Proleukin®, Novartis) in IFA s.c. on day 1 (together with tumour cells) and every 21 days till the end of the experiment. Pamidronate (10 mg/kg body weight) was applied in the indicated groups at day 1 i.v. and every 21 days i.p. Outgrowing tumours were visualized in vivo by Biospace bioluminescent imaging (BLI). Mice were anesthetized by isoflurane before they received an intraperitoneal injection (100 μl) of 25 mg/ml Beetle Luciferin (Promega). Bioluminescence images were acquired and analyzed with M3Vision software (Photon Imager, Biospace Laboratory).

Results

Anti-Tumour Reactivity of Individual γ9δ2T-Cell Clones

To investigate whether individual γ9δ2T-cell clones mediate differential activity against tumour cells compared to the parental γ9δ2T-cell population, γ9δ2T-cells from a healthy donor were cloned by limiting dilution and tested against a broad panel of tumour cells in an IFNγ ELISpot. High variability in tumour recognition in terms of specificity and functional avidity was observed between individual γ9δ2T-cell clones (cl); compared to the original bulk population, cl5 and cl13 produced twice as many IFNγ spots in response to Daudi and selectively generated significant amounts IFNγ when challenged with K562, BT549 and MCF-7. In contrast, cl3 and cl15 recognized solely Daudi cells. Surface expression of γ9δ2TCR, NKG2D, CD158a, NKAT-2 and NKB-1 was examined.

Anti-Tumour Reactivity Mediated by Individual γ9δ2TCRs

To elucidate differences among γ9δ2TCRs of tumour-reactive clones, sequences of wildtype (wt) γ9- and δ2-TCR chains of cl3 (γ9-cl3$_{wt}$/δ2-cl3$_{wt}$) and cl5 (γ9-cl5$_{wt}$/δ2-cl5$_{wt}$) were determined and aligned with γ9δ2TCR G115. All three γ9δ2TCRs differed in their CDR3 domains: 1-3 amino acids between position γ109 and γ111 in γCDR3 and 4-8 amino acids between δ108 and δ112 in δCDR3. To determine whether distinct γ9δ2TCRs mediate differential anti-tumour reactivity, individual γ9δ2TCR chains were cloned into the retroviral vector pBullet and linked to a selection marker as described. The wildtype-combinations γ9-cl3$_{wt}$/δ2-cl3$_{wt}$, γ9-cl5$_{wt}$/δ2-cl5$_{wt}$ and γ9-G115$_{wt}$/δ2-G115$_{wt}$ were transduced into peripheral blood αβT-cells, selected by antibiotics and further expanded. γ9δ2TCR G115 (γ9-G115$_{wt}$/δ2-G115$_{wt}$) served as control, as did cells transduced with an empty vector cassette (mock). γ9δ2TCR-transduced T-cells showed similar γ9δ2TCR expression and were tested for their lytic activity against the tumour target Daudi in a $^{51}$Cr-release assay (FIG. 1A). T-cells expressing γ9-cl3$_{wt}$/δ2-cl3, had a 50 percent reduced ability to lyse tumour cells (p<0.01), whereas T-cells with γ9-cl5$_{wt}$/δ2-cl5$_{wt}$ were nearly twice as potent (p<0.01) as the control γ9-G115$_{wt}$/δ2-G115$_{wt}$. To determine whether the phenotypes of γ9δ2TCR-transduced cells with decreased or increased functional avidity are also present on cytokine level a pamidronate-titration assay was performed. Pamidronate treatment of Daudi cells blocks the mevalonate-pathway downstream to IPP causing the accumulation of IPP and an enhanced cytokine secretion of responsive T-cells. To exclude NK-like activation CD4$^+$ γ9δ2TCR-transduced T-cells, which lack the expression of major NK-receptors like NKG2D, were selected by MACS-sorting. Transductants were tested at different concentrations of pamidronate against the tumour target Daudi. Mock-transduced T-cells which underwent equivalent stimulation but express an irrelevant αβTCR served as control. IFNγ secretion was measured by ELISA and the half maximal effective concentration (EC50) was calculated (FIG. 1B). In line with changes observed for lytic capacity, T-cells transduced with γ9-cl3$_{wt}$/δ2-cl3$_{wt}$ secreted lower amounts of IFNγ (max. 600 pg/ml), while T-cells expressing γ9-cl5$_{wt}$/δ2-cl5$_{wt}$ produced higher levels of IFNγ (max. 1300 pg/ml) at all pamidronate concentrations, relative to control γ9-G115$_{wt}$/δ2-G115$_{wt}$ (max. 800 pg/ml). Despite different plateaus in IFNγ secretion, all selected mutants and the wildtype control had a comparable pamidronate-EC50 (~30 pg/ml). These results indicate that distinct γ9δ2TCR clones mediate different functional avidity and the high variability among parental γ9δ2T-cell clones in tumour recognition seems to be substantially regulated by the CDR3 domains of individual γ9δ2T-cell receptors.

Combinatorial-γδTCR-chain-exchange (CTE) as rapid method to modulate functional avidity of engineered T-cells.

To make the above determination, we devised a strategy named combinatorial-γδTCR-chain-exchange (CTE), which results in the expression of newly combined γ9- and δ2-TCR chains on engineered T-cells. During this process, γ9-G115$_{wt}$ was combined with δ2-cl3$_{wt}$ or δ2-cl$_{wt}$ and δ2-G115$_{wt}$ with γ9-cl3$_{wt}$ or γ9-cl5$_{wt}$. These combinations were retrovirally transduced into αβT-cells. In all transductants equivalent γδTCR expression was detected while the endogenous αβTCR was clearly down regulated. This resulted not only into a nearly abolished allo-reactivity of αβT-cells expressing γ9-G115$_{wt}$/δ2-G115$_{wt}$ but also of selected CTE-engineered αβT-cells when compared to mock-transduced cells. Thus, reactivity of CTE-engineered T-cells primarily depends on expressed OTCRs and not on residual endogenous αβTCRs. Next, transductants were functionally tested against the tumour target Daudi in a $^{51}$Cr-release assay (FIG. 1C). The exchange of γ9- or δ2-chains indeed caused notable differences. Compared to the original TCR γ9-G115$_{wt}$/δ2-G115$_{wt}$, the combination of γ9-G115$_{wt}$/δ2-cl3$_{wt}$, γ9-G115$_{wt}$/δ2-cl5$_{wt}$ or γ9-cl5$_{wt}$/δ2-G115$_{wt}$ mediated 40 to 70 percent increased specific lysis of tumour cells (all p<0.05). The same magnitude of recognition was observed when IFNγ production of CD4$^+$ γδTCR-transduced T-cells was tested in a pamidronate titration assay (FIG. 1D). Moreover, only the combination γ9-cl$_{wt}$/δ2-G115$_{wt}$ led to decreased IFNγ production of transduced cells at all pamidronate concentrations (max. 100 pg/ml), while all other CTE-γ9δ2 TCRs mediated an increased IFNγ-secretion (max. ≥1000 pg/ml) as compared to control TCR γ9-G115$_{wt}$/δ2-G115$_{wt}$ (max. 800 pg/ml). Equal pamidronate-EC50s of ~30 pg/ml were calculated for all responsive γ9δ2 TCR-transduced cells.

To determine whether cell-cell interaction influences the response-kinetics differently than pamidronate stimulation, CTE-γ9δ2 TCR γ9-G115$_{wt}$/δ2-cl5$_{wt}$ which mediates improved functional avidity and control TCR γ9-G115$_{wt}$/δ2-G115$_{wt}$ were tested in an effecter-to-target ratio (E:T) titration assay (FIG. 1E), and an E:T-50 was calculated. Interestingly, T-cells with γ9-G115$_{wt}$/δ2-cl5$_{wt}$ responded differently with an E:T-50 of 0.3:1, compared to an E:T-50 of 1:1 calculated for control cells expressing γ9-G115$_{wt}$/δ2-G115$_{wt}$. To test whether the interaction between different TCRs and ligands—thus the affinity—is indeed increased, cell-cell conjugates between Daudi and T-cells expressing either potentially high (γ9-G115$_{wt}$/δ2-cl5$_{wt}$) or low (γ9-cl3$_{wt}$/δ2-G115$_{wt}$) affinity TCRs were measured by flow cytometry. Significantly more cell-cell interactions were observed when γ9-G115$_{wt}$/δ2-cl5$_{wt}$ was expressed as compared to γ9-cl3$_{wt}$/δ2-G115$_{wt}$ and mock-transduced T-cells (FIG. 1F). This effect did not depend on the presence of pamidronate. G115$_{wt}$/δ2-cl5$_{wt}$ is therefore a high affinity γ9δ2TCR. Hence, CTE is an efficient method to rapidly engineer γ9δ2TCRs with increased affinity, mediating improved functional avidity in transduced T-cells.

Figure 2:
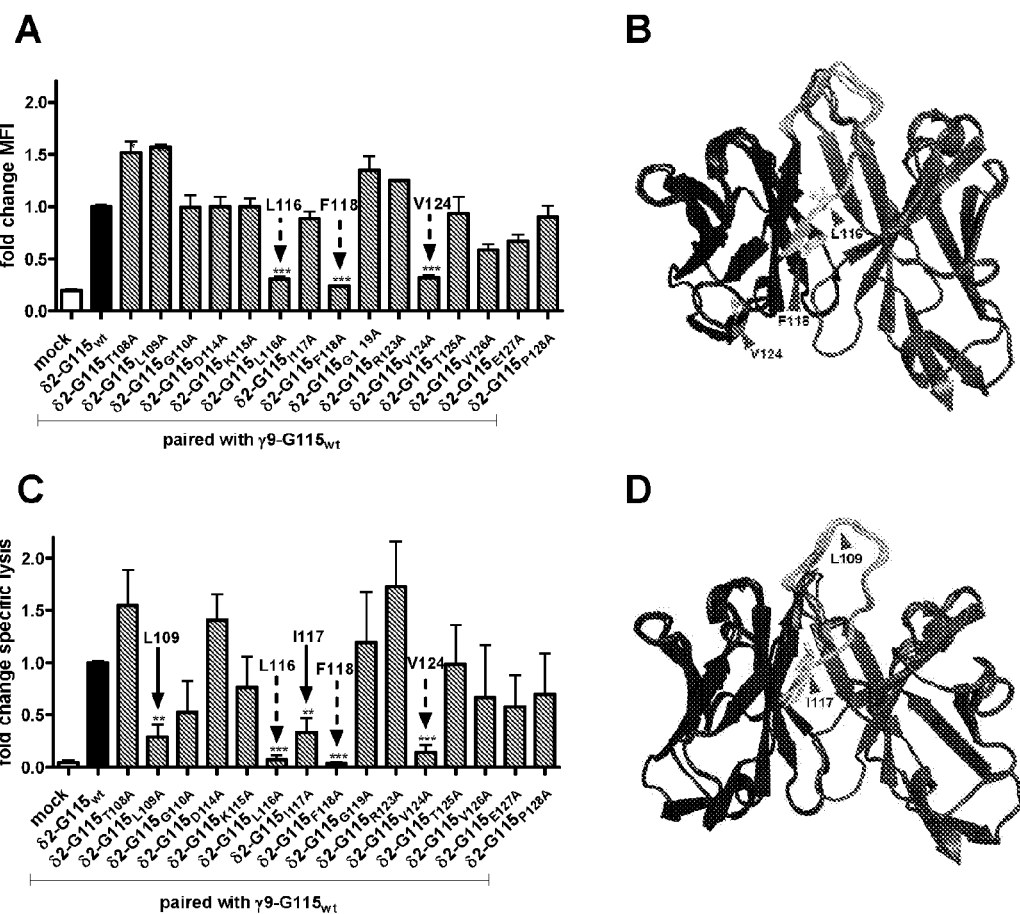

Residues in δCDR3 and Jδ1 are involved in γ9δ2TCR stability and in mediating functional avidity of engineered αβT-cells To elucidate the molecular requirements of δCDR3 to mediate optimal functional avidity, alanine-mutagenesis of a model δCDR3 (clone G115) was performed including the whole Jδ1 segment, as important residues have also been reported within Jγ1. During an initial screening, five sequence areas were found to either influence TCR expression or functional avidity of γ9δ2 TCR transduced T-cells. To clarify the degree to which single residues are responsible for impaired γ9δ2 TCR expression and lower TCR-mediated functional avidity, single alanine mutations were generated. The mutated and wildtype δ2-G115 chains were expressed in combination with γ9-G115$_{wt}$ in αβT-cells and tested for γ9δ2TCR expression using a δ2-chain specific antibody (FIG. 2A). Three single alanine mutations caused a 70 percent lower TCR expression when compared to the unmutated δ2-G115$_{wt}$, namely δ2-G115$_{L116A}$, δ2-G115$_{F118A}$ and δ2-G115$_{V124A}$ (Table 3). Comparable results were observed using antibodies directed against the γ9-chain or the constant domain of the γδTCR, indicating the importance of δ2-G115$_{L116}$, δ2-G115$_{F118}$ and δ2-G115$_{V124}$ for stable TCR expression. The crystal structure of γ9δ2 TCR G115 supports our findings: δ2-G115$_{L116}$, δ2-G115$_{F118}$ and δ2-G115$_{V124}$ are located in hydrophobic cores (FIG. 2B) and could thus be crucial for the structural stability of the γ9δ2 TCR G115.

To address the impact of single alanine mutations on functional avidity, a $^{51}$Cr-release assay was performed (FIG. 2C). Transductants with low TCR expression (δ2-G115$_{L116A}$, δ2-G115$_{F118A}$ and δ2-G115$_{V124A}$) could not tumour cells effectively, as they demonstrated an 80 percent lower lytic capacity when compared to cells transduced with δ2-G115$_{wt}$. T-cells with mutation δ2-G115$_{L109A}$ and δ2-G115$_{I117A}$ (Table 3) properly expressed the TCR but showed a 70 percent reduced lytic activity when compared to δ2-G115$_{wt}$ expressing cells. Similar results were obtained when TCR mutants were transduced into CD4$^+$ Jurkat cells and IL-2 production was measured (data not shown). Reduction of lytic activity was also seen when alanine substitutions δ2-G115$_{L109A}$ and δ2-G115$_{I117A}$ were introduced into the δ2-chain of γδTCR clone 3. These results indicate that not only residue δL109, but also δI117 in δCDR3 may be generally important for γ9δ2 TCRs to mediate functional avidity (FIG. 2D). Sequence alignments between δ2-chains of clones 3, 5 and G115 indicated that δL109 and δI117 may be conserved (Table 2).

Figure 3:
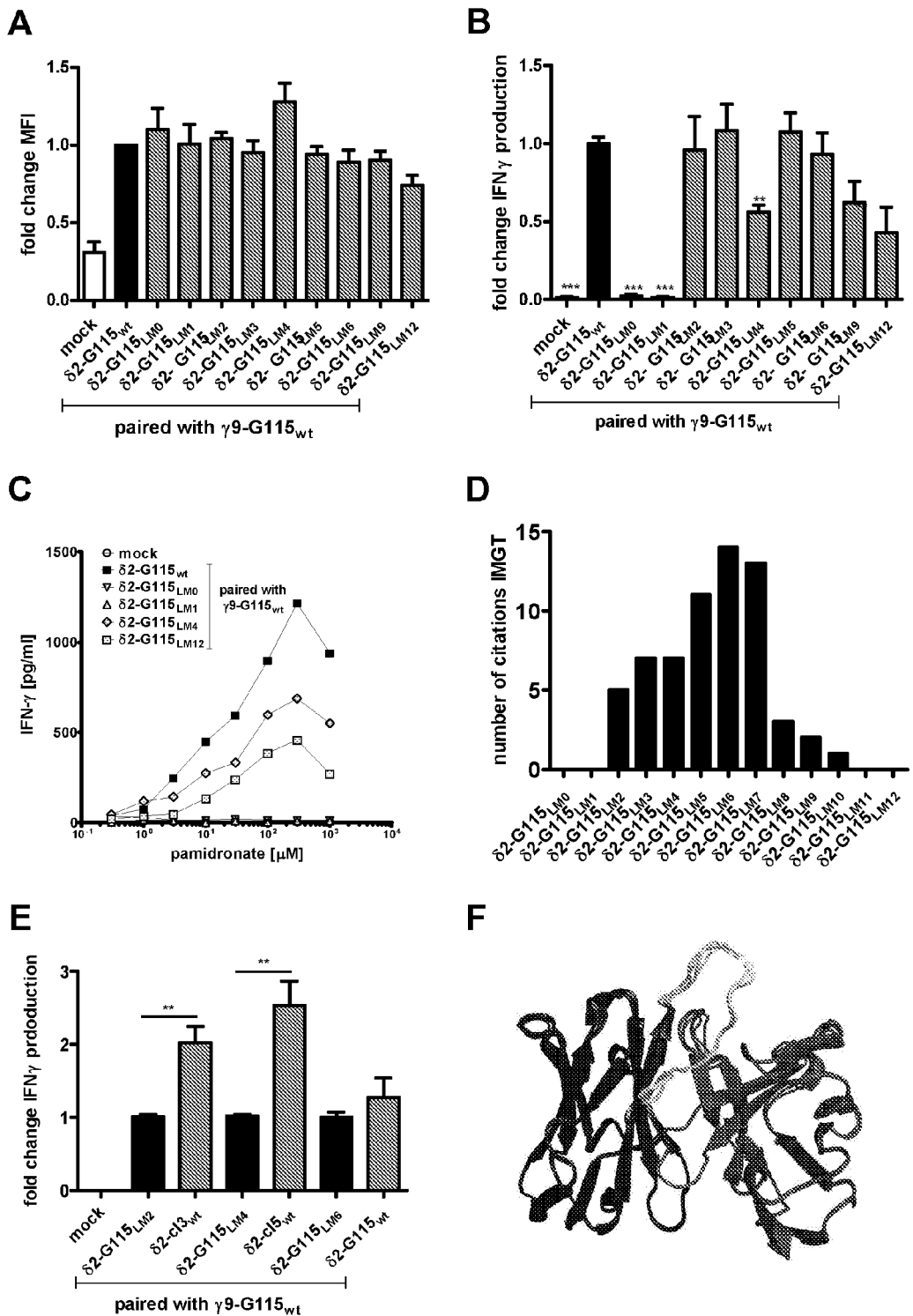

(δ2-G115$_{LM2, 3, 5, 6, 9}$) induced comparable amounts of IFNγ in engineered T-cells relative to transductants expressing δ2-G115$_{wt}$. Mutants with functional impairment (δ2-G115$_{LM0,1,4,12}$, Table 4) were further tested against increasing pamidronate concentrations and an EC50 was calculated. Despite different plateaus in maximal IFNγ secretion, all selected δ2-G115$_{LM}$ transduced cells and the wildtype control had a comparable pamidronate-EC50 (~30 pg/ml) (FIG. 3C). Length mutations were also studied in γCDR3 of γ9δ2 TCR G115 by engineering stretches of 1-6 alanines between γ9-G115$_{E108}$ and γ9-G115$_{E111.1}$ (γ9-G115$_{1-6}$). However, this did not affect functional avidity.

This indicates that considerable alanine stretches within γ9 and δ2CDR3 domains can be tolerated. However, too

TABLE 3

CDR3 sequence of γ9δ2TCR G115, clone 3 and clone 5

γCDR3

| γ9-chain | 104 | 105 | 106 | 107 | 108 | 109 | 110 | 111 | 111.1 | 112.1 | 112 | 113 | 114 | 115 | 116 | 117 | 118 | 119 | 120 | 121 | 122 | 123 | 124 | 125 | 126 | 127 |
|---|---|---|---|---|---|---|---|---|---|---|---|---|---|---|---|---|---|---|---|---|---|---|---|---|---|---|
| | | | | | | | | | | | | | | | | | JγP | | | | | | | | | |
| γ9-cl3$_{wt}$ | C | A | L | W | E | E | - | - | E | L | G | K | K | I | K | V | F | G | P | G | T | K | L | I | I | T |
| γ9-cl5$_{wt}$ | C | A | L | W | E | I | - | Q | E | L | G | K | K | I | K | V | F | G | P | G | T | K | L | I | I | T |
| γ9-G115$_{wt}$ | C | A | L | W | E | A | Q | Q | E | L | G | K | K | I | K | V | F | G | P | G | T | K | L | I | I | T |

δCDR3

| δ2-chain | 104 | 105 | 106 | 107 | 108 | 109 | 110 | 111 | 111.1 | 112.2 | 112.1 | 112 | 113 | 114 | 115 | 116 | 117 | 118 | 119 | 120 | 121 | 122 | 123 | 124 | 125 | 126 | 127 | 128 |
|---|---|---|---|---|---|---|---|---|---|---|---|---|---|---|---|---|---|---|---|---|---|---|---|---|---|---|---|---|
| | | | | | | | | | | | | | | | | | | Jδ1 | | | | | | | | | | |
| δ2-cl3$_{wt}$ | C | A | C | D | L | L | G | - | - | - | - | Y | T | D | K | L | I | F | G | K | G | T | R | V | T | V | E | P |
| δ2-cl5$_{wt}$ | C | A | C | D | A | L | K | R | - | - | T | D | T | D | K | L | I | F | G | K | G | T | R | V | T | V | E | P |
| δ2-G115$_{wt}$ | C | A | C | D | T | L | G | M | G | G | E | Y | T | D | K | L | I | F | G | K | G | T | R | V | T | V | E | P |

The table above shows an alignment of three clones and the numbering listed is in accordance with IGMT. The γ9-G115$_{wt}$ sequence listed corresponds to amino acids C117-T142 of amino acid sequence SEQ ID NO. 1.γ112.1L, of either clone 3, 5 or G115$_{wt}$ thus corresponds to L126 of amino acid sequence SEQ ID NO. 1. The δ2-G115wt sequence listed corresponds to amino acids C111-C138 of amino acid sequence SEQ ID NO. 2. Hence, as this alignment shows, corresponding CDR3 regions of clones 3 and 5 can easily be identified via alignment.

Influence of CDR3 Length on Functional Avidity of γ9δ2TCR Transduced T-Cells

Alanine substitutions during alanine-scanning mutagenesis of γ9δ2 TCR G115 could replace large parts of the δCDR3 domain without functional consequences. That raises the possibility that the crucial factor for the differing functional avidities of distinct γ9δ2 TCR combinations may also involve the relative length between the functionally important residues δ2-G115$_{L109}$ and the structurally important residue δ2-G115$_{L116}$. Therefore, different δ2-G115 length mutants were generated. Since the triple δ2-G115$_{T113-K115}$ is also important for stable surface expression (data not shown), nine length mutants (δ2-G115$_{LM}$) with 0 to 12 alanine between δ2-G115$_{L109}$ and δ2-G115$_{T113}$ were generated and equally expressed in αβT-cells, again in combination with γ9-G115$_{wt}$ (FIG. 3A). To test the functional avidity of δ2-G115$_{LM}$ transduced T-cells, CD4$^+$ TCR-transduced T-cells were selected by MACS-sorting and an IFNγ ELISA in response to Daudi was performed in the presence of pamidronate (FIG. 3B). Engineered T-cells expressing δ2-G115$_{LM0}$ and δ2-G115$_{LM1}$ were unable to produce IFNγ and T-cells expressing δ-G115$_{LM4}$ or δ-G115$_{LM12}$ secreted only about half the amount of IFNγ compared to δ2-G115$_{wt}$ transduced cells. All other mutants short and very long alanine stretches between δ2-G115$_{L109}$ and δ2-G115$_{T113}$ in particular, as well as stretches with four alanines, may be associated with reduced or absent function of a γ9δ2 TCR (FIGS. 3B and 3C).

Consequences for the Physiological γ9δ2 T-Cell Repertoire

The ImMunoGeneTics (IMGT) database was searched for reported stretches between γ9-G115$_{E109}$ and γ9-G115$_{E111.1}$ as well as δ2-G115$_{L109}$ and δ2-G115$_{T113}$. A preferential length for reported γ9-chains was found for CDR3 regions corresponding to γ9-G115$_{LM2}$ and γ9-G115$_{LM3}$, but shorter stretches were also reported. In contrast, δ2-chains with short δCDR3 domains, such as δ2-G115$_{LM1}$ or δ2-G115$_{LM0}$, were not reported (FIG. 3D), in line with our observation that such chains may not be functional. The majority of listed γ9δ2TCRs contain δCDR3 lengths which correspond to δ2-G115$_{LM5,6,7}$. These findings support a preference to select γ9δ2TCRs with a δCDR3 length of 5-7 residues between δ2-G115$_{L109}$ and δ2-G115$_{T113}$. Nevertheless, individual sequence differences can still play a role in γ9δ2TCR mediated functional avidity.

Influence of the CDR3 Sequence on γ9δ2TCR Mediated Functional Avidity.

To test both the length and sequence of δCDR3 for mediating optimal functional avidity, γ9δ2TCR length mutants δ2-G115$_{LM2}$, δ2-G115$_{LM4}$, and δ2-G115$_{LM6}$ were transduced into αβT-cells in combination with γ9-G115$_{wt}$. IFNγ-secretion of transductants in response to Daudi was compared to cells transduced with wildtype sequences from δ2-cl3$_{wt}$ (corresponds in length to δ2-G115$_{LM2}$) δ2-cl5$_{wt}$ (corresponds in length to δ2-G115$_{LM4}$), and δ2-G115$_{wt}$ (corresponds in length to δ2-G115$_{LM6}$) (Table 3). T-cells transduced with δ2-G115$_{LM6}$ and δ2-G115$_{wt}$ did not differ in the amount of cytokine secretion, all other combinations of wildtype chains showed a more than two-fold increase in IFNγ when compared to the length mutant that selectively contained alanines (FIG. 3E). These results were confirmed when the lytic capacity of transduced cells was tested. The sequence in δCDR3 may therefore also be a significant factor for the functioning of a γ9δ2TCR.

Accordingly, the sequential importance of γCDR3 was studied. Thereby, γ9-G115$_{LM1-3}$ were transduced into T-cells in combination with δ2-G115$_{wt}$. IFNγ-secretion of transductants in response to Daudi was compared to cells transduced with γ9-cl3$_{wt}$ (corresponds in length to γ9-G115$_{LM1}$), γ9-cl5$_{wt}$ (corresponds in length to γ9-G115$_{LM2}$) and γ9-G115$_{wt}$ (corresponding to γ9-G115$_{LM3}$) (Table 3). T-cells expressing γ9-cl3$_{wt}$/δ2-G115$_{wt}$ selectively produced lower amounts of IFNγ when compared to their equivalent γ9-G115$_{LM1}$ (FIG. 4A). Previously, the same γ9δ2TCR combination was also found to mediate reduced functional avidity (FIGS. 1C and 1D). Loss of activity could be restored to normal levels (referred to γ9δ2TCR G115$_{wt}$) by mutating γCDR3$_{E109}$ in γ9-cl3$_{wt}$ to γCDR3$_{A109}$, demonstrating that a single change in the variable sequence of γ9CDR3 may be sufficient to regulate functional avidity of γ9δ2TCR transduced T-cells tested here.

In summary, the length and sequence of the δ2CDR3 domain between L109 and T113 (Table 3) can play a role in γ9δ2 TCR-mediated functional avidity. In addition, the individual sequence between E108 and E111.1 in γ9CDR3 may hamper activity of a γ9δ2TCR, and in G115 γCDR3$_{A109}$ may be of importance for ligand interaction (Table 3 and FIG. 4B). Combined, this provides a rationale for CTE-engineered γ9δ2TCRs but also for random mutagenesis within both γ9 and δ2CDR3 regions.

CTE-Engineered T-Cells as a Tool for Cancer Immunotherapy.

CTE-engineered γ9δ2 TCRs with increased activity against tumour cells are interesting candidates for TCR-gene therapeutic strategies. Changes in functional avidity mediated by CTE-γ9δ2 TCRs may constitute a unique phenomenon of a defined γ9δ2 TCR pair in response to the B-lymphoblastic cell line Daudi, or this may be a general response to most tumour targets. Therefore, CTE-γ9δ2 TCRs that mediated increased (γ9-G115$_{wt}$/δ2-cl5$_{wt}$) or reduced (γ9-cl3$_{wt}$/δ2-G115$_{wt}$) activity were tested against various tumours in an IFNγELISA in the presence of pharmacological concentrations of pamidronate (10 μM) (FIG. 5A). Tumour reactivity was significantly increased against a whole range of different tumour entities including other hematological cancers such as RPMI8226/S, OPM2, LME1 (all multiple myeloma), K562 (myelogenous leukemia) as well as solid cancer cell lines such as Saos2 (osteosarcoma), MZ1851RC (renal cell carcinoma), SCC9, Fadu (head and neck cancer), MDA-MB231, MCF7, BT549 (all breast cancer), and SW480 (colon carcinoma) when taking advantage of γ9-G115$_{wt}$/δ2-cl5$_{wt}$ as compared to γ9-G115$_{wt}$/δ2-G115$_{wt}$ and was significantly reduced or even absent for all other targets using γ9-cl3$_{wt}$/δ2-G115$_{wt}$. Moreover, CTE-engineered T-cells with increased activity against tumour cells still did not show any reactivity towards healthy tissue such as PBMCs and fibroblasts. Superior lytic activity of T-cells engineered with γ9-G115$_{wt}$/δ2-cl5$_{wt}$ was also observed for hematological cancer cells like RPMI8226/S, OPM2, L363 as well as solid cancer cell lines Saos2, MZ1851RC, SCC9, MDA-MB231, and SW480 when compared to control T-cells expressing γ9-G115$_{wt}$/δ2-G115$_{wt}$ (FIG. 5B). Therefore, CTE-engineered γ9δ2 TCRs can provide higher anti-tumour response against a broad panel of tumour cells while not affecting normal tissue, and thus have the potential to increase efficacy of TCR-engineered T-cells.

To assess the potential clinical impact of CTE-engineered γ9δ2 TCRs, it was tested whether an increased efficacy of CTE-γ9δ2 TCRs may also be present when primary blasts of AML patients are chosen as targets. Therefore, CTE-γ9δ2 TCR transduced T-cells were tested against 11 primary AML blasts and healthy CD34$^+$ progenitor cells in an IFNγ-ELISpot (FIG. 5C). Transductants expressing γ9-G115$_{wt}$/δ2-cl5$_{wt}$ recognized 8 out of 11 primary AML samples equally or superiorly compared to control γ9-G115$_{wt}$/δ2-G115$_{wt}$. Furthermore, CD34$^+$ progenitor cells were not recognized by T-cells expressing either γ9-G115$_{wt}$/δ2-cl5$_{wt}$ or γ9-G115$_{wt}$/δ2-G115$_{wt}$. In light of these findings, CTE-engineered TCR γ9-G115$_{wt}$/δ2-cl5$_{wt}$ appears to be a promising candidate for clinical application.

Finally, to demonstrate that CTE-γ9δ2 TCRs are safe and function with increased efficacy when compared to the original constructs in vivo, adoptive transfer of T-cells engineered with CTE-TCRs was studied in a humanized mouse model: protection against outgrowth of Daudi or RPMI8226/S in Rag2$^{-/-}$γc$^{-/-}$ double knockout mice. Therefore peripheral blood αβT-cells were transduced with CTE-TCR γ9-G115$_{wt}$/δ2-cl5$_{wt}$ or control TCR γ9-G115$_{wt}$/δ2-G115$_{wt}$. CTE-TCR transduced T-cells showed similar expression of homing markers including L-selectin and CCR7. Irradiated Rag2$^{-/-}$γc$^{-/-}$ mice received luciferase-transduced Daudi (0.5×10$^6$) or RPMI8226/S cells (5×10$^6$) and 10$^7$ CTE-engineered T-cells by intravenous injection. The frequency of T-cell infusion was reduced to one intravenous injection relative to our previously reported model were two infusions were given in order to test superiority of CTE-TCR transduced T-cells under suboptimal conditions. Consequently, this resulted in loss of protection with TCR G115$_{wt}$-engineered T-cells when tumour growth was measured by bioluminescence imaging (BLI) (FIGS. 6A and 6B). However, CTE-engineered T-cells expressing γ9-G115$_{wt}$/δ2-cl5$_{wt}$ clearly reduced tumour outgrowth for Daudi (20.000 counts/min, day 42, n=4) and RPMI8226/S (80.000 counts/min, day 35, n=7) as compared to TCR G115$_{wt}$-engineered T-cells (Daudi: 180.000 counts/min, day 42; RPMI8226/S: 210.000 counts/min, day 35). T-cells could be found in the periphery until 1-2 weeks after infusion in mice, but frequency of T-cells did not correlate with tumour regression. Finally, in the rapidly lethal Daudi-model only mice treated with CTE-engineered T-cells had a significant increased overall survival of ~2 months relative to mice treated with T-cells expressing γ9-G115$_{wt}$/δ2-G115$_{wt}$ (FIG. 6C). These results indicate that CTE-engineered γ9δ2 TCRs efficiently mediate anti-tumour reactivity in vivo, which points to CTE as a potential tool to optimize γ9δ2TCRs for clinical application.

In table 4 below, results with regard to methods performed according to the invention are listed. The delta-CDR3 domain was tested for TCR function by alanine-mutagenesis (Table 3, mutation) of the CDR3-domain (including the whole J-segment) of the well studied clone G115 and amino acids that may be relevant for TCR stability and TCR function are found. In addition, the amino acid sequence length (Table 3, length mutations) between γE108 and γE111.1 of the γ9-chain and between δL109 and δT113 of the δ2-chain was tested. The individual sequences of γ9-CDR3 and δ2-CDR3 domains are of importance for function (Table 3, sequence). By CTE-engineering the γ9- and δ2-TCR chains of clone G115 was combined with γ9- and δ2-TCR chains of clone 3 and clone 5, respectively. CTE-engineering resulted in 4 newly designed γδTCRs. The original TCRs and the new CTE-engineered TCRs (Table 3, combination) were transduced into αβT-cells and tested for their function

TABLE 4

Effect of mutations and chain-combinations on γ9δ2-TCR function

| γ9δ2TCR | | expression | IFN-γ response | cytotoxic activity |
|---|---|---|---|---|
| | mutation | | | |
| γ9-G115/δ2-G115 | original | +++ | +++ | +++ |
| γ9-G115/δ2-G115$_{T108A}$ | δT108 → δA108 | ++++ | +++ | +++ |
| γ9-G115/δ2-G115$_{L109A}$ | δL109 → δA109 | ++++ | − | − |
| γ9-G115/δ2-G115$_{G110A}$ | δG110 → δA110 | +++ | nd | +++ |
| γ9-G115/δ2-G115$_{M111A, G111.1A, G112.2A}$ | δM111 → δA111<br>δG111.1 → δA111.1<br>δG112.2 → δA112.2 | +++ | +++ | +++ |
| γ9-G115/δ2-G115$_{E112.1A, Y112A, T113A}$ | δE112.1 → δA112.1<br>δY112 → δA112<br>δT113 → δA113 | +++ | +++ | +++ |
| γ9-G115/δ2-G115$_{D114A}$ | δD114 → δA110 | +++ | nd | +++ |
| γ9-G115/δ2-G115$_{K115A}$ | δK115 → δA110 | +++ | nd | +++ |
| γ9-G115/δ2-G115$_{L116A}$ | δL116 → δA116 | − | nd | − |
| γ9-G115/δ2-G115$_{I117A}$ | δI117 → δA117 | +++ | − | − |
| γ9-G115/δ2-G115$_{F118A}$ | δF118 → δA118 | − | nd | − |
| γ9-G115/δ2-G115$_{G119A}$ | δG119 → δA119 | +++ | nd | +++ |
| γ9-G115/δ2-G115$_{K120A, G121A, T122A}$ | δK120 → δA120<br>δG121 → δA121<br>δT122 → δA122 | +++ | +++ | +++ |
| γ9-G115/δ2-G115$_{R123A}$ | δR123 → δA123 | +++ | nd | +++ |
| γ9-G115/δ2-G115$_{V124A}$ | δV124 → δA124 | − | nd | − |
| γ9-G115/δ2-G115$_{T125A}$ | δT125 → δA125 | +++ | nd | +++ |
| γ9-G115/δ2-G115$_{V126A}$ | δV126 → δA126 | +++ | nd | +++ |
| γ9-G115/δ2-G115$_{E127A}$ | δE127 → δA127 | +++ | nd | +++ |
| γ9-G115/δ2-G115$_{P128A}$ | δP128 → δA128 | +++ | nd | +++ |
| γ9-G115/δ2-G115$_{deletion\ T113-K115}$ | deletion δT113, δD114 & δK115 | + | nd | nd |
| | length mutation | | | |
| γ9-G115$_{LM1}$/δ2-G115 | γE108-1A-γE111.1 | +++ | +++ | +++ |
| γ9-G115$_{LM2}$/δ2-G115 | γE108-2A-γE111.1 | +++ | +++ | +++ |
| γ9-G115$_{LM3}$/δ2-G115 | γE108-3A-γE111.1 | +++ | +++ | +++ |
| γ9-G115$_{LM4}$/δ2-G115 | γE108-4A-γE111.1 | +++ | +++ | +++ |
| γ9-G115$_{LM5}$/δ2-G115 | γE108-5A-γE111.1 | +++ | +++ | +++ |
| γ9-G115$_{LM6}$/δ2-G115 | γE108-6A-γE111.1 | +++ | +++ | +++ |
| γ9-G115/δ2-G115$_{LM0}$ | δL109-0A-δT113 | +++ | − | − |
| γ9-G115/δ2-G115$_{LM1}$ | δL109-1A-δT113 | +++ | − | − |
| γ9-G115/δ2-G115$_{LM2}$ | δL109-2A-δT113 | +++ | +++ | +++ |
| γ9-G115/δ2-G115$_{LM3}$ | δL109-3A-δT113 | +++ | +++ | +++ |
| γ9-G115/δ2-G115$_{LM4}$ | δL109-4A-δT113 | +++ | + | +++ |
| γ9-G115/δ2-G115$_{LM5}$ | δL109-5A-δT113 | +++ | +++ | +++ |
| γ9-G115/δ2-G115$_{LM6}$ | δL109-6A-δT113 | +++ | +++ | +++ |
| γ9-G115/δ2-G115$_{LM9}$ | δL109-9A-δT113 | +++ | ++ | +++ |
| γ9-G115/δ2-G115$_{LM12}$ | δL109-12A-δT113 | +++ | + | +++ |
| | sequence | | | |
| γ9-G115/δ2-cl3 | original | +++ | +++ | +++ |
| γ9-G115/δ2-G115$_{LM2}$ | δL109-2A-δT113 | +++ | + | + |
| γ9-G115/δ2-cl5 | original | +++ | +++ | +++ |
| γ9-G115/δ2-G115$_{LM4}$ | δL109-4A-δT113 | +++ | + | + |
| γ9-cl3/δ2-G115 | original | +++ | nd | + |
| γ9-cl3$_{E109A}$/δ2-G115 | γE109 → γA109 | +++ | nd | +++ |
| | combination | | | |
| γ9-G115/δ2-G115 | original | +++ | +++ | +++ |
| γ9-cl3/δ2-cl3 | original | +++ | + | + |
| γ9-cl5/δ2-cl5 | original | +++ | +++++ | +++++ |
| γ9-cl3/δ2-G115 | CTE | +++ | + | + |
| γ9-G115/δ2-cl3 | CTE | +++ | ++++ | ++++ |
| γ9-cl5/δ2-G115 | CTE | +++ | ++++ | ++++ |
| γ9-G115/δ2-cl5 | CTE | +++ | +++++ | +++++ |

SEQ LISTING

| SEQ ID | description | type |
|---|---|---|
| 1 | γ9-T-cell receptor chain (G115) | AA |
| 2 | δ2-T-cell receptor chain (G115) | AA |
| 3 | γ9-T-cell receptor chain CDR3 region (G115) | AA |
| 4 | δ2-T-cell receptor chain CDR3 region (G115) | AA |
| 5 | γ9-T-cell receptor chain (G115) | NA |
| 6 | δ2-T-cell receptor chain (G115) | NA |
| 7 | γ9-T-cell receptor chain (clone 3) | NA |
| 8 | γ9-T-cell receptor chain (clone 3) | AA |
| 9 | δ2-T-cell receptor chain (clone 3) | NA |
| 10 | δ2-T-cell receptor chain (clone 3) | AA |
| 11 | γ9-T-cell receptor chain (clone 5) | NA |
| 12 | γ9-T-cell receptor chain (clone 5) | AA |
| 13 | δ2-T-cell receptor chain (clone 5) | NA |
| 14 | δ2-T-cell receptor chain (clone 5) | AA |
| 15 | ALKRTD | AA |
| 16 | ALWEIQELGKKIKV | AA |
| 17 | ACDALKRTDTDKLI | AA |
| 18 | ACDLLGYTDKLI | AA |
| 19 | TLGMGGEY | AA |
| 20 | IQ | AA |
| 21 | AQQ | AA |
| 22 | LLGY | AA |

AA = amino acid sequence
NA = nucleic acid sequence

The invention claimed is:

1. A γ9δ2T-cell receptor, or a fragment thereof, comprising a γ9-T-cell receptor chain comprising a γ9-CDR3 region, wherein the amino acid sequence of the γ9-CDR3 region corresponding to amino acid residues 122-124 of SEQ ID NO. 1 is IQ (SEQ ID NO. 20) and a δ2-T-cell receptor chain comprising a δ2-CDR3 region wherein the amino acid sequence of the δ2-CDR3 region corresponding to amino acid residues 115-122 of SEQ ID NO. 2 is ALKRTD (SEQ ID NO. 15), and wherein said γ9δ2T-cell receptor, or fragment thereof is exogenously expressed in an engineered cell.

2. A γ9δ2T-cell receptor, or a fragment thereof, comprising: a γ9-T-cell receptor chain comprising a γ9-CDR3 region, wherein the amino acid sequence of the γ9-CDR3 region corresponds to the amino acid sequence of SEQ ID NO. 16, and a δ2-T-cell receptor chain comprising a δ2-CDR3 region wherein the amino acid sequence of the δ2-CDR3 region corresponds to the amino acid sequence of SEQ ID NO. 17, and wherein said γ9δ2T-cell receptor, or fragment thereof is exogenously expressed in an engineered cell.

3. The γ9δ2T-cell receptor or fragment thereof according to claim 1, wherein:
the amino acid sequence of the γ9-CDR3 region corresponding to amino acid residues 118-121 of the amino acid sequence of SEQ ID NO. 1 is ALWE,
the amino acid sequence of the γ9-CDR3 region corresponding to amino acid residues 125-132 of the amino acid sequence of SEQ ID NO. 1 is ELGKKIKV,
the amino acid sequence of the δ2-CDR3 region corresponding to amino acid residues 112-114 of the amino acid sequence of SEQ ID NO. 2 is ACD, and
the amino acid sequence of the δ2-CDR3 region corresponding to amino acid residues 123-127 of the amino acid sequence of SEQ ID NO. 2 is TDKLI; and
wherein said γ9δ2T-cell receptor, or fragment thereof is exogenously expressed in an engineered cell.

4. The γ9δ2T-cell receptor, or fragment thereof, according to claim 1, wherein the γ9-T-cell receptor chain comprises an amino acid sequence having at least 95% sequence identity with the amino acid sequence comprising amino acid residues 21-315 of SEQ ID NO. 1, wherein the δ2-T-cell receptor chain comprises an amino acid sequence having at least 95% sequence identity with the amino acid sequence comprising amino acid residues 20-292 of SEQ ID NO. 2, and wherein said g9d2T-cell receptor can mediate anti-tumor response in a cell expressing the same.

5. The γ9δ2T-cell receptor, or fragment thereof, according to claim 1, wherein the γ9-T-cell receptor chain comprises the amino acid sequence of SEQ ID NO. 12 and wherein the δ2-T-cell receptor chain comprises the amino acid sequence of SEQ ID NO. 14.

6. A conjugate comprising a soluble fragment of the γ9δ2T-cell receptor according to claim 1, comprising said γ9-CDR3 region and said δ2-T-cell δ2-CDR3 region, linked to an agent.

7. The conjugate according to claim 6, wherein the agent is selected from the group consisting of a diagnostic agent, a therapeutic agent, an anti-cancer agent, a chemical, a nanoparticle, a chemotherapeutic agent and a fluorochrome.

8. An engineered T cell, genetically modified to express a γ9δ2T-cell receptor, wherein said γ9δ2T-cell receptor comprises:
a γ9-T-cell receptor chain comprising a γ9-CDR3 region, wherein the amino acid sequence of the γ9-CDR3 region corresponding to amino acid residues 122-124 of SEQ ID NO. 1 is IQ (SEQ ID NO. 20); and
a δ2T-cell receptor chain comprising a δ2-CDR3 region wherein the amino acid sequence of the δ2-CDR3 region corresponding to amino acid residues 115-122 of SEQ ID NO. 2 is ALKRTD (SEQ ID NO. 15).

9. The engineered T cell according to claim 8, wherein the T cell comprises:
a) an isolated nucleic acid sequence or isolated nucleic acid sequences encoding:
i) a δ2-T-cell receptor chain, or fragment thereof, comprising a δ2-CDR3 region, wherein the amino acid sequence of the δ2-CDR3 region corresponding to amino acid residues 115-122 of the amino acid sequence of SEQ ID NO. 2 is ALKRTD (SEQ ID NO. 15); and
ii) a γ9-T-cell receptor chain, or fragment thereof, comprising a γ9-CDR3 region, wherein the amino acid sequence of the γ9-CDR3 region corresponding to amino acid residues 122-124 of SEQ ID NO. 1 is IQ (SEQ ID NO. 20),
b) a genetic construct or genetic constructs comprising the isolated nucleic acid sequence(s) or
c) a retroviral vector or retroviral vectors comprising the genetic construct(s).

10. The engineered T cell according to claim 8, wherein the γ9-T-cell receptor chain comprises the amino acid sequence of SEQ ID NO. 12 and wherein the δ2-T-cell receptor chain comprises the amino acid sequence of SEQ ID NO. 14.

11. A medicament comprising one selected from the group consisting of:
a) γ9δ2T-cell receptor, or fragment thereof, comprising:
i) a γ9-T-cell receptor chain comprising a γ9-CDR3 region, wherein the amino acid sequence of the γ9-CDR3 region corresponding to amino acid residues 122-124 of SEQ ID NO. 1 is IQ (SEQ ID NO. 20) and a δ2-T-cell receptor chain comprising a δ2-CDR3 region wherein the amino acid sequence of the δ2-CDR3 region corresponding to amino acid residues 115-122 of SEQ ID NO. 2 is ALKRTD (SEQ ID NO. 15); or
ii) a γ9-T-cell receptor chain comprising a γ9-CDR3 region, wherein the amino acid sequence of the γ9-CDR3 region corresponds to SEQ ID NO. 16 and a δ2-T-cell receptor chain comprising a δ2-CDR3 region wherein the amino acid sequence of the δ2-CDR3 region corresponds to SEQ ID NO. 17;
b) a conjugate comprising a soluble fragment of the γ9δ2T-cell receptor, comprising the γ9-CDR3 and the δ2-T-cell δ2-CDR3 region, linked to an agent;
c) an isolated nucleic acid sequence or isolated nucleic acid sequences encoding:
i) the δ2-T-cell receptor chain, or fragment thereof, wherein the δ2-CDR3 region corresponding to amino acid residues 115-122 of SEQ ID NO. 2 is ALKRTD (SEQ ID NO. 15),
ii) the γ9-T-cell receptor chain, or fragment thereof, wherein the amino acid sequence of the γ9-CDR3 region corresponding to amino acid residues 122-124 of the amino acid sequence of SEQ ID NO. 1 is IQ (SEQ ID NO. 20), or
iii) the γ9δ2T-cell receptor, or fragment thereof;
d) a genetic construct or genetic constructs comprising the isolated nucleic acid sequence(s);
e) a retroviral vector or retroviral vectors comprising the genetic construct(s); and
f) an engineered T cell, genetically modified to express the γ9δ2T-cell receptor.

12. The medicament according to claim 11, wherein the medicament is useful for the treatment of cancer.

13. An engineered γ9δ2T-cell receptor, or a fragment thereof, comprising a γ9-T-cell receptor chain comprising a γ9-CDR3 region, wherein the amino acid sequence of the γ9-CDR3 region corresponding to amino acid residues 122-124 of SEQ ID NO. 1 is modified and a δ2-T-cell receptor chain comprising a δ2-CDR3 region wherein the amino acid sequence of the δ2-CDR3 region corresponding to amino acid residues 115-122 of SEQ ID NO. 2 is modified, wherein the combinations of the amino acid modifications within the γ9δ2T-cell receptor, or a fragment thereof, are as listed in Table 1.

14. A γ9δ2T-cell receptor, or a fragment thereof, comprising: a γ9-T-cell receptor chain comprising a γ9-CDR3 region according to claim 12, wherein the amino acid sequence of the γ9-CDR3 region corresponding to amino acid residues 122-124 of the amino acid sequence of SEQ ID NO. 1 is AQQ (SEQ ID NO. 21), and a δ2-T-cell receptor chain comprising a δ2-CDR3 region wherein the amino acid sequence of the δ2-CDR3 region corresponding to amino acid residues 115-122 of the amino acid sequence of SEQ ID NO. 2 is ALKRTD (SEQ ID NO. 15).

15. A γ9δ2T-cell receptor, or a fragment thereof, comprising: a γ9-T-cell receptor chain comprising a γ9-CDR3 region according to claim 12, wherein the amino acid sequence of the γ9-CDR3 region corresponding to amino acid residues 122-124 of the amino acid sequence of SEQ ID NO. 1 is IQ (SEQ ID NO. 20), and a δ2-T-cell receptor chain comprising a δ2-CDR3 region wherein the amino acid sequence of the δ2-CDR3 region corresponding to amino acid residues 115-122 of the amino acid sequence of SEQ ID NO. 2 is TLGMGGEY (SEQ ID NO. 19).

16. A γ9δ2T-cell receptor, or a fragment thereof, comprising: a γ9-T-cell receptor chain comprising a γ9-CDR3 region according to claim 12, wherein the amino acid sequence of the γ9-CDR3 region corresponding to amino acid residues 122-124 of the amino acid sequence of SEQ ID NO. 1 is AQQ (SEQ ID NO. 21), and a δ2-T-cell receptor chain comprising a δ2-CDR3 region wherein the amino acid sequence of the δ2-CDR3 region corresponding to amino acid residues 115-122 of the amino acid sequence of SEQ ID NO. 2 is LLGY (SEQ ID NO. 22).

17. A γ9δ2T-cell receptor, or fragment thereof, according to claim 13, wherein the γ9-T-cell receptor chain comprises an amino acid sequence having at least 95% sequence identity with the amino acid sequence comprising amino acid residues 21-315 of SEQ ID NO. 1, wherein the δ2-T-cell receptor chain comprises an amino acid sequence having at least 95% sequence identity with the amino acid sequence comprising amino acid residues 20-292 of SEQ ID NO. 2, wherein the amino acid sequence of the γ9-CDR3 region corresponding to amino acid residues number 122-124 of SEQ ID NO. 1, and the amino acid sequence of the δ2-CDR3 region corresponding to amino acid residues 115-122 of SEQ ID NO. 2 are as listed in Table 1, and wherein said g9d2T-cell receptor can mediate anti-tumor response in a cell expressing the same.

18. A receptor, or fragment thereof comprising a γ9-T-cell receptor chain comprising a γ9-CDR3 region, wherein the amino acid sequence of the γ9-CDR3 region corresponding to amino acid residues 122-124 of SEQ ID NO. 1 is IQ (SEQ ID NO. 20) and a δ2-T-cell receptor chain comprising a δ2-CDR3 region wherein the amino acid sequence of the δ2-CDR3 region corresponding to amino acid residues 115-122 of SEQ ID NO. 2 is ALKRTD (SEQ ID NO. 15), and wherein said receptor, or fragment thereof is exogenously expressed in an engineered cell.

19. A receptor, or fragment thereof, comprising a γ9-T-cell receptor chain comprising a γ9-CDR3 region, wherein the amino acid sequence of the γ9-CDR3 region corresponding to amino acid residues 122-124 of SEQ ID NO. 1 is modified and a δ2-T-cell receptor chain comprising a δ2-CDR3 region wherein the amino acid sequence of the δ2-CDR3 region corresponding to amino acid residues 115-122 of SEQ ID NO. 2 is modified, wherein the combinations of the amino acid modifications within the receptor, or fragment thereof are as listed in Table 1.

* * * * *